US012582302B2

(12) United States Patent
Anwar et al.

(10) Patent No.: US 12,582,302 B2
(45) Date of Patent: Mar. 24, 2026

(54) APPARATUS, SYSTEMS AND METHODS FOR IN VIVO IMAGING

(71) Applicant: The Regents of the University of California, Oakland, CA (US)

(72) Inventors: Moshiur M. Anwar, San Francisco, CA (US); Catherine Park, San Francisco, CA (US); Bernhard Boser, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 128 days.

(21) Appl. No.: 17/639,722

(22) PCT Filed: Sep. 4, 2020

(86) PCT No.: PCT/US2020/049474
§ 371 (c)(1),
(2) Date: Mar. 2, 2022

(87) PCT Pub. No.: WO2021/126323
PCT Pub. Date: Jun. 24, 2021

(65) Prior Publication Data
US 2023/0143102 A1      May 11, 2023

Related U.S. Application Data

(60) Provisional application No. 62/895,757, filed on Sep. 4, 2019.

(51) Int. Cl.
*A61B 1/05* (2006.01)
*A61B 1/00* (2006.01)
(Continued)

(52) U.S. Cl.
CPC ............ *A61B 1/05* (2013.01); *A61B 1/00009* (2013.01); *A61B 1/000094* (2022.02);
(Continued)

(58) Field of Classification Search
CPC . A61B 1/05; A61B 1/00009; A61B 1/000094; A61B 1/043; A61B 1/0684; A61B 1/3132; A61B 5/0091; A61B 2560/0418; A61B 1/0676; A61B 5/0071; A61B 5/0077; A61B 5/0084; A61B 5/0086; A61B 5/6848; A61B 10/0041
See application file for complete search history.

(56) References Cited

U.S. PATENT DOCUMENTS

| | | | |
|---|---|---|---|
| 11,419,543 B1* | 8/2022 | Peyman ................. | C07K 16/22 |
| 2011/0309236 A1* | 12/2011 | Tian ..................... | H10F 30/288 |
| | | | 257/E31.097 |

(Continued)

FOREIGN PATENT DOCUMENTS

WO      2019027370 A1    2/2019

*Primary Examiner* — Md K Talukder
(74) *Attorney, Agent, or Firm* — Fredrikson & Byron, P.A.

(57) ABSTRACT

The disclosed apparatus, systems and methods relate to the use of optical nanoparticles in the illumination and imaging of tissues such as cancer tissues. Optical nanoparticles such as upconverting nanoparticles can be introduced into a patient and illuminated at a first time and wavelength and then imaged at a second time and wavelength to improve resolution and reduce imager size.

26 Claims, 32 Drawing Sheets

(51) Int. Cl.
    *A61B 1/04*           (2006.01)
    *A61B 1/06*           (2006.01)
    *A61B 1/313*         (2006.01)
    *A61B 5/00*           (2006.01)

(52) U.S. Cl.
    CPC ............ *A61B 1/043* (2013.01); *A61B 1/0684*
             (2013.01); *A61B 1/3132* (2013.01); *A61B*
                                 *5/0091* (2013.01)

(56)                 References Cited

U.S. PATENT DOCUMENTS

| | | | |
|---|---|---|---|
| 2012/0220870 A1* | 8/2012 | Gambhir | B82Y 30/00 |
| | | | 600/431 |
| 2012/0326055 A1 | 12/2012 | Wilson et al. | |
| 2015/0182118 A1* | 7/2015 | Bradbury | A61P 17/00 |
| | | | 600/431 |
| 2016/0325112 A1* | 11/2016 | Zweig | A61L 31/022 |
| 2016/0374559 A1* | 12/2016 | Anwar | A61K 49/0067 |
| | | | 600/478 |
| 2018/0042483 A1* | 2/2018 | Bardhan | G01J 3/2823 |
| 2018/0256208 A1* | 9/2018 | Altschul | A61B 5/14532 |
| 2019/0000320 A1* | 1/2019 | Anwar | A61B 5/0084 |
| 2021/0052330 A1* | 2/2021 | Kiselyov | A61B 8/5269 |
| 2021/0169334 A1* | 6/2021 | Kodandaramaiah | |
| | | | A61B 5/14546 |
| 2022/0218265 A1* | 7/2022 | Shepard | A61B 5/0084 |
| 2023/0143102 A1* | 5/2023 | Anwar | A61B 1/0684 |
| | | | 382/128 |

\* cited by examiner aUCNP
intratumoral
injection

Intratumoral aUCNP
intensity and
spectrum vs time

Risk of Recurrence with MRD

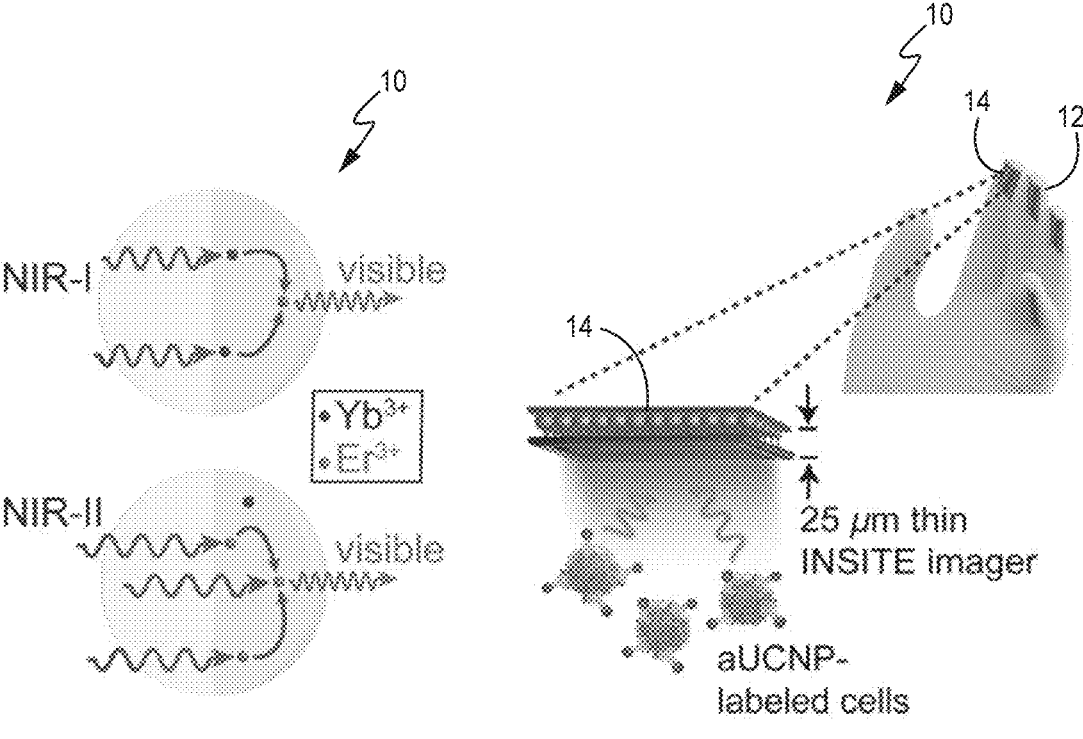
FIG. 5A            FIG. 5B
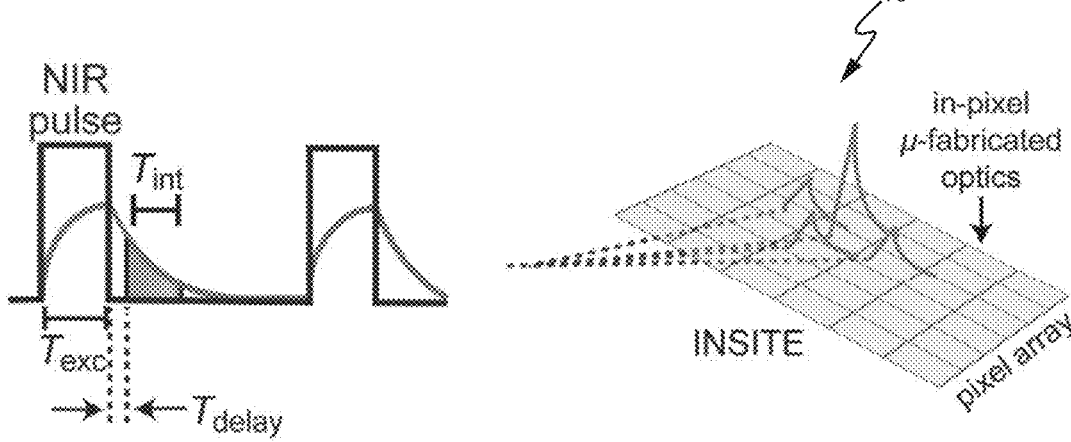
FIG. 5C            FIG. 5D

Time-Resolved Imaging

FIG. 13C aUCNP Characterization Setup

Time-Resolved Imaging
of μ-well of aUCNPs 980 nm Laser   PDMS
μ-wells

Imager Chip

Imaging Chip (Zoomed)

←PDMS
←aUCNPs
in well

Chip Image

Spatial Resolution of Cells
Improves with Thinner Imager

Florescence
Contact Imager
Requires Filter
and Waveguide
(500 μm thick),

No Optics =
Thinner Imager =
Higher Resolution

Imaging of Excised Tumor

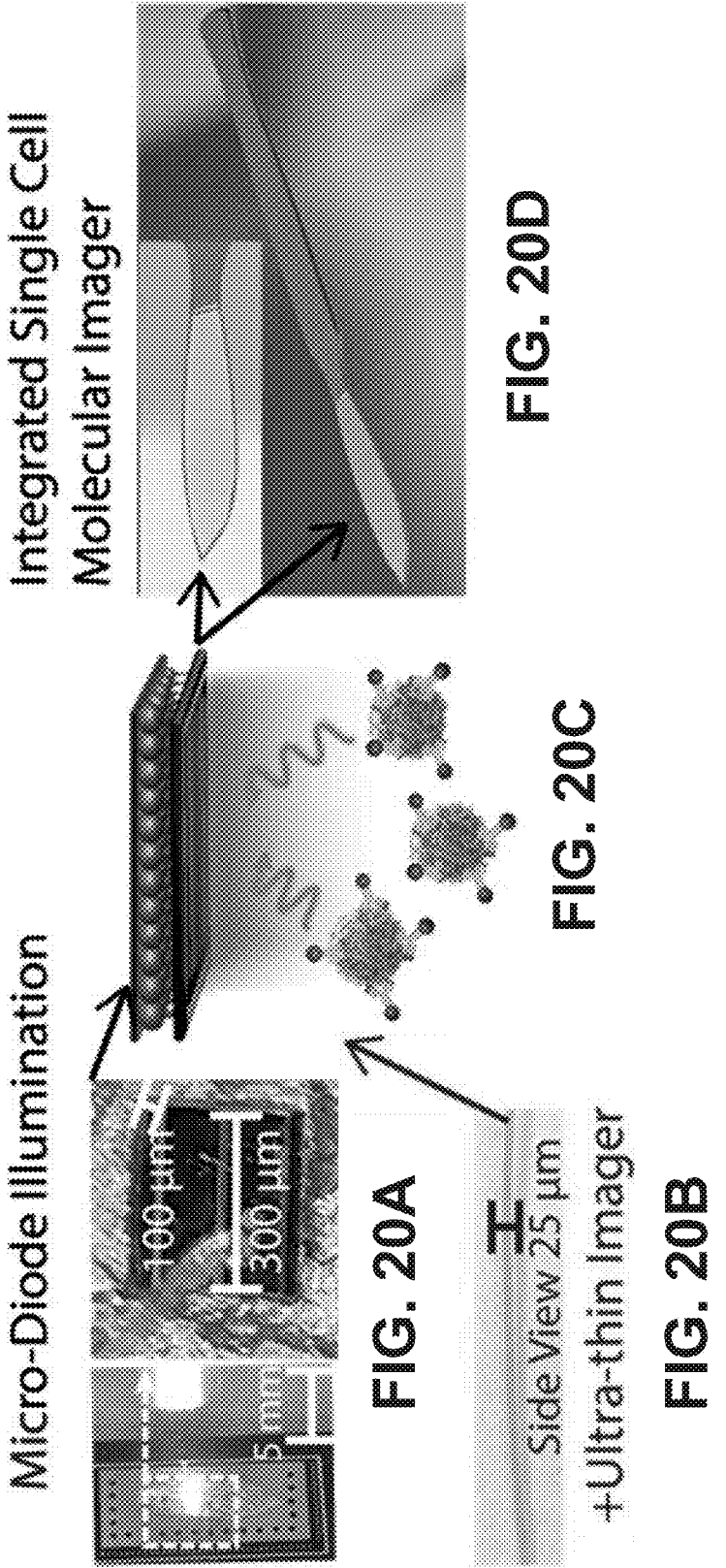

Hair (~40 μm)

APPARATUS, SYSTEMS AND METHODS FOR IN VIVO IMAGING

CROSS-REFERENCE TO RELATED APPLICATION(S)

This application claims priority to International PCT Application No. PCT/US20/49474, filed on Sep. 4, 2020, which claims priority to U.S. Provisional Application No. 62/895,757 filed Sep. 4, 2019, which is hereby incorporated by reference in its entirety under 35 U.S.C. § 119(e).

GOVERNMENT SUPPORT

This invention was made with government support under grant no. R21 EB027238 awarded by The National Institutes of Health and grant no. W81XWH-15-1-0531 awarded by The Defense Advanced Research Projects Agency. The government has certain rights in the invention.

TECHNICAL FIELD

The disclosed technology relates generally to surgical devices and techniques, and in particular, to the devices, methods, and design principles for an intra-operative imaging system for visualizing microscopic disease. This has implications in the minimally disruptive treatment of a variety of diseases.

BACKGROUND

The disclosure relates to apparatus, systems and methods for an intra-operative imaging system for visualizing microscopic disease. Undetected microscopic residual disease and lymph node involvement is common in curative cancer surgeries and significantly increases cancer recurrence, driving the need for molecularly image guided cancer surgery. Successful treatment of early stage cancer depends on complete resection of all disease, both gross and microscopic, yet microscopic foci of cancer cells, unable to be seen or felt, are all too often left behind, significantly increasing the chance of cancer returning across disease sites, and in select cases, reduces survival. This often prompts additional therapy consisting of broad areas of empiric re-excision and/or radiation to reduce this increased risk, causing significant toxicity (and cost), while potentially missing the residual disease altogether. This poses a particular challenge in breast cancer, where clinicians and patients must weigh the morbidity associated with empirically resecting normal healthy tissue (mastectomy) against using more focal surgery (with radiation), but risk leaving tumor cells behind with significant consequences. Microscopic residual disease (MRD) doubles the local recurrence (LR) rate, from 15% to 30% over 15 years, increasing breast cancer deaths, leading to a recommendation for re-excision in many cases. In breast cancer, this occurs with striking frequency: 20-40% of 140,000 women who undergo lumpectomy annually in the US, are found to have MRD, leading to ~37,000 reoperations. FIG. 2 is a bar graph depicting the risk of recurrence with MRD in various cancer types. Ultrasound, specimen radiography, MarginProbe and the like lack sensitivity for MRD. Blind, empiric removal of additional tissue is still inadequate: a recent phase III randomized clinical trial comparing lumpectomy with or without empiric shave margins, still showed a 20% rate of MRD after shave excision (albeit reducing the 34% rate of MRD with lumpectomy alone) attesting to the importance of not only identifying MRD, but determining its exact location for re-resection.

Despite the advent of molecularly targeted imaging agents, image guided surgeries remain hindered by the intraoperative imagers themselves. This project unlocks the power of inorganic optical nanoparticles to significantly advance in vivo intraoperative molecular imaging for cancer by developing an ultra-thin (<200 μm) molecular imaging skin, integrated on any surgical instrument, for real-time, single-cell visualization of tumor cells intraoperatively.

Undetected lymph node involvement possesses an even greater challenge, as these lymph nodes lie in minimally dissected areas, often several millimeters below the tissue surface. Left untreated, they often recur as distant metastases, leading to death, as evidenced by several studies showing a survival benefit to empiric irradiation of lymph nodes (targeting MRD) in high risk patients. However, undetected MRD in lower risk patients continues to go untreated, and RT empirically delivered to uninvolved nodes in even high-risk patients causes significant morbidity (pneumonitis, lymphedema >30-50% in patients with surgery+RT).

The lack of precision, individualized knowledge of tumor cell location in vivo results in empirically administered large surgical or post-operative radiotherapy fields, causing significant toxicity while potentially still leaving tumor cells untreated. Although fluorescently labeled targeted molecular agents accurately label single cancer cells in vivo, the constraints on intraoperative imagers placed by organic fluorophores remain the limiting reagent: the small Stokes shift and absorption cross-section require high-performance optical filters and lenses. The bulk and rigidity of these optics limits current intraoperative instrumentation: to line of sight vision, missing the majority of the resection cavity and lymph node basins; to operation from outside the tumor bed, significantly decreasing sensitivity; and precludes manipulation within the small surgical cavities inherent in modern minimally invasive oncologic procedures.

Thus, there is a need in the art for improved devices, systems and methods for the imaging of microscopic tumor foci, which cannot be seen or felt, are often left behind in the tumor bed and lymph nodes during cancer surgery, increasing cancer recurrence and metastases, respectively.

BRIEF SUMMARY

Discussed herein are various devices, systems and methods relating to a microscopic imaging system. Various of the disclosed examples utilize the long UCNP time-constants on the order of 100-1000 μs, readily detectable by modern high-speed silicon-based ICs, to implement time-resolved imaging, enabling a filterless high-density imaging array to cover a large tissue area with high spatial resolution. Without the need for optics, the silicon imager is thinned and can be scaled to a wide range of dimensions. It can be coupled to a thin LED or laser diode and placed directly on the tissue surface, achieving unprecedented intraoperative mobility, increasing both sensitivity and spatial resolution through micron proximity to tumor cells, obtaining single-cell resolution. Various implementations include back-side illumination, where in the long wavelength light goes through the back of the silicon-based imager because silicon is effectively transparent at wavelengths above 1100 nm and directly illuminates tissue through the chip itself.

In Example 1, an imaging system, comprising an imaging chip; and a composition comprising at least one optical nanoparticle wherein the imaging chip is constructed and arranged to detect light emission from that nanoparticle.

In Example 2, the imaging system of claim 1, wherein the imaging chip is configured for time-resolved imaging.

In Example 3, the imaging system of claim 2, wherein the imaging system further comprises an illumination device.

In Example 4, the imaging system of claim 1, wherein the imaging chip is filterless.

In Example 5, the imaging system of claim 1, wherein the at least one optical nanoparticle has a luminescence lifetime greater than 1 microsecond.

In Example 6, the imaging system of claim 1, wherein the at least one optical nanoparticle has a luminescence lifetime greater than 10 microseconds.

In Example 7, the imaging system of claim 1, wherein the at least one optical nanoparticle comprises an upconverting nanoparticle (UCNP).

In Example 8, the imaging system of claim 1, wherein the at least one optical nanoparticle upconverts near-infrared light to higher energy light.

In Example 9, the imaging system of claim 1, wherein the imaging chip is lensless.

In Example 10, the imaging chip of claim 1, wherein the imaging chip is between about 25 microns and about 1 mm thick.

In Example 11, the imaging system of claim 1, wherein the imaging chip is between about 1 mm^2 and about 40 cm^2 wide.

In Example 12, the imaging system of claim 1, wherein the imaging chip is fitted to a medical device.

In Example 13, the imaging system of claim 12, wherein the medical device is a scalpel, probe, drop in probe for laparoscopic or robotic surgery, or glove.

In Example 14, the imaging system of claim 1, further comprising an illumination array.

In Example 15, the imaging system of claim 14, wherein the illumination array is an array of LED or laser diodes surrounding the chip.

In Example 16, the imaging system of claim 14, wherein the illumination array is an array of LEDs, laser diodes, or fiber optics configured for through illumination.

In Example 17, the imaging system of claim 14, wherein the through illumination is patterned.

In Example 18, the imaging system of claim 1, wherein the optical nanoparticle is conjugated to a molecule targeted toward a cell type of interest.

In Example 19, the imaging system of claim 18, wherein the molecule is a protein, antibody, component of an antibody, or small molecule.

In Example 20, the imaging system of claim 19, wherein the cell type of interest is a cancer cell.

In Example 21, a method of imaging disease tissue, comprising: introducing a composition comprising at least one optical nanoparticle into tissue; illuminating the at least one optical nanoparticle; and recording luminescence of the at least one optical nanoparticle with an imaging chip.

In Example 22, the method of claim 21, wherein the at least one optical is illuminated at a first wavelength and emits light at a second wavelength.

In Example 23, the method of claim 22, wherein the illumination wavelength is longer than the emitted wavelength.

In Example 24, the method of claim 21, wherein the luminescence is recoded after the at least one optical nanoparticle is illuminated.

In Example 25, the method of claim 21, wherein at least one optical nanoparticle is an upconverting nanoparticle.

In Example 26, the method of claim 21, further comprising performing ratiometric imaging to determine the depth of the at least one optical nanoparticle.

In Example 27, the method of claim 21, wherein at least one optical nanoparticle is conjugated to a molecule or protein that binds to a target cell.

In Example 28, the method of claim 21, wherein the protein is an antibody or derivative.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure. Accordingly, the drawings and detailed description are to be regarded as illustrative in nature and not restrictive.

BRIEF DESCRIPTION OF THE DRAWINGS

FIG. 5 is an overview of the imaging of upconverting nanoparticles according to one implementation. (A) shows the absorption, transfer, and emission in Yb3+/Er3+-based aUCNPs following either NIR-I (980 nm) or NIR-II (1550 nm) excitation. (B) is a cartoon of imaging platform directly integrated onto surfaces, such surgical glove. (C) is a diagram of the time-resolved image acquisition scheme. Texc, pulse excitation time; Tint, emission signal integration time; Tdelay, time gating delay. (D) shows angle-selective gratings used to achieve lensless image acquisition and block obliquely incident background light.

Figures 13A, 13B, 13C:
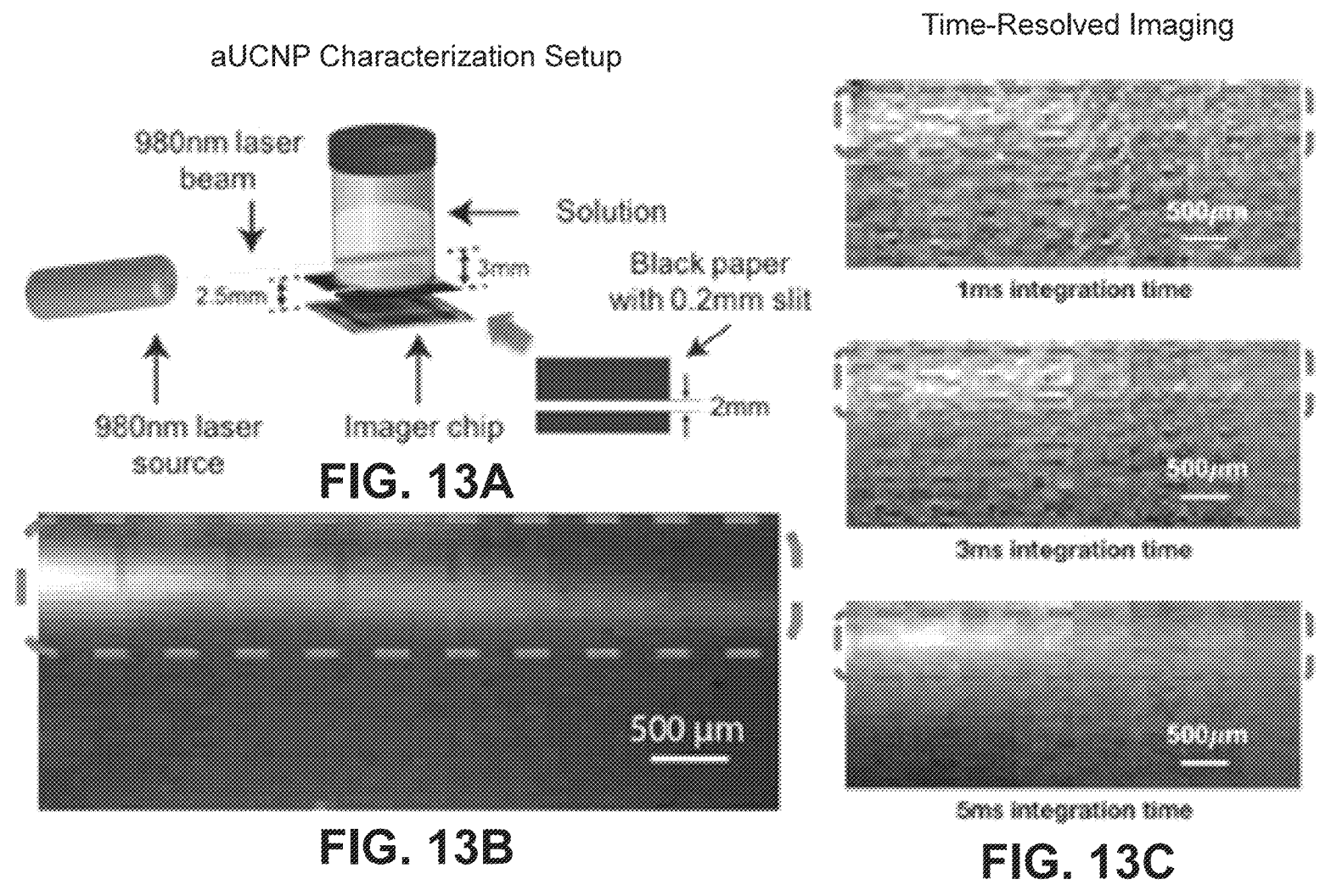

FIG. 13 (a) is aUCNP-TRI array setup, (b) imaging a slit of aUCNPs (1000 images), (c) Single image with increasing integration times (1, 3, 5 ms) showing SNR and SBR of 4 with single 5 ms image.

FIG. 20 shows device integration, according to one implementation. (a) shows 100 μm-thin microdiodes affixed to the back of the CMOS imager chip (c), which is thinned to 25 μm (b) and affixed to surgical instrumentation (d).

DETAILED DESCRIPTION

Figure 1A:
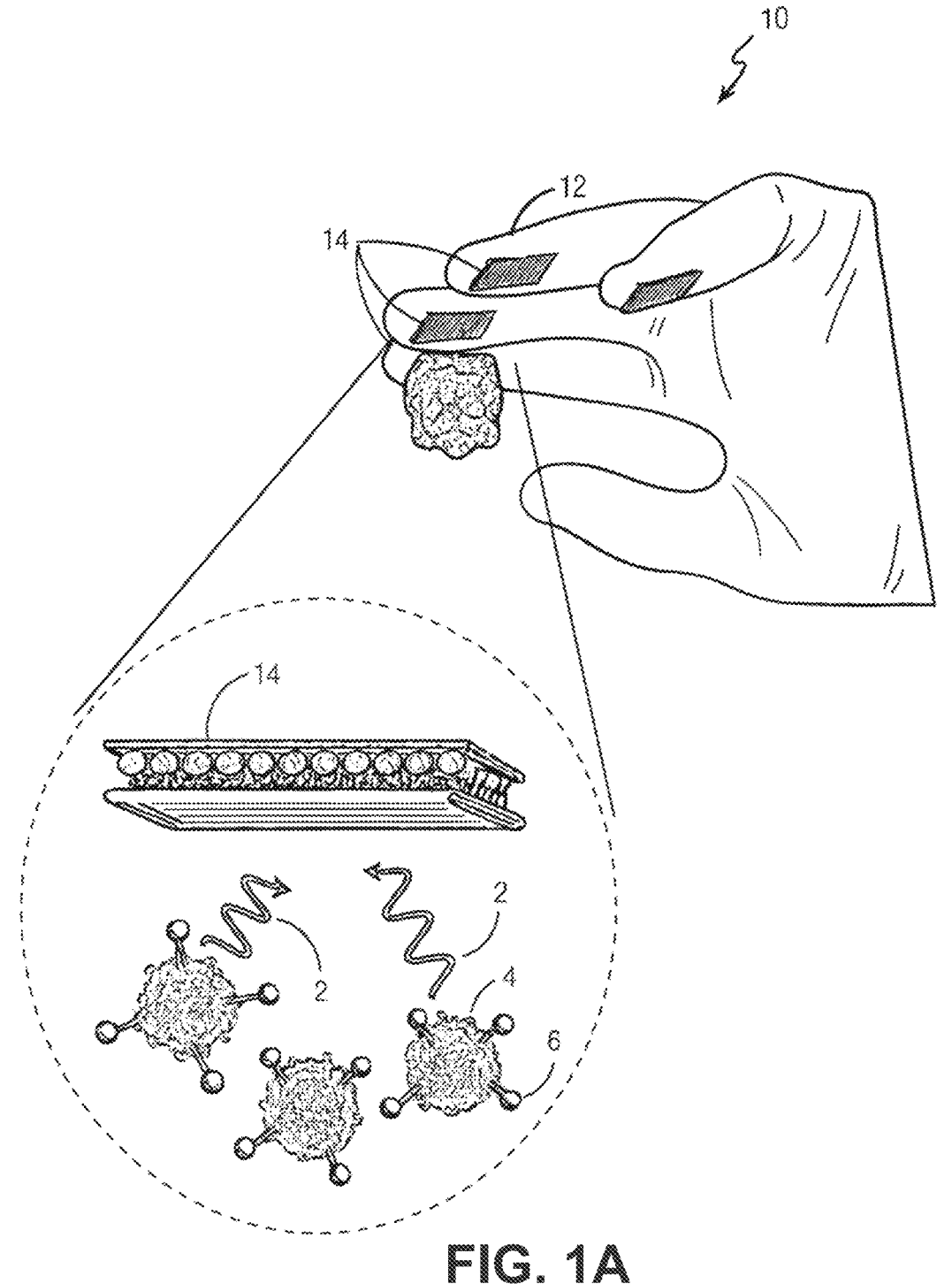
FIG. 1A-1H depict several views of the components and implementations of the system.

The various systems and devices disclosed herein relate to devices for use in medical procedures. More specifically, various embodiments relate to imaging devices, systems and methods for visualizing microscopic residual disease (MRD) and microscopic lymph node involvement (mLNI) in an intraoperative environment. Certain exemplary implementations relate to imaging systems, devices, and methods for visualizing microscopic breast and prostate cancer. It is understood that the various embodiments of the system and related methods disclosed herein can be incorporated into or used with any other known medical devices, systems and methods, including those disclosed in co-pending U.S. application Ser. No. 15/687,205, filed Aug. 25, 2017 and entitled "Apparatus, Systems and Methods for Intraoperative Imaging," which is a continuation-in-part of U.S. application Ser. No. 15/074,614, filed Mar. 18, 2016 entitled "Methods, Systems, And Devices For Imaging Microscopic Tumors," which was filed under 35 U.S.C. § 371 and claims the benefit of International PCT Patent Application No. PCT/US14/56788, filed on Sep. 22, 2014, and U.S. Provisional Application 61/880,750, filed Sep. 20, 2013, and entitled "Methods, Systems, And Devices For Imaging Microscopic Tumors," and U.S. Provisional Application No. 62/379,416 filed Aug. 25, 2016 and entitled "Apparatus, Systems and Methods for Intraoperative Imaging," each of which is hereby incorporated by reference in its entirety. While the system is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

Prior art imagining approaches have limitations. Despite the introduction of targeted molecular agents for cancer surgery guidance, the requisite bulky and rigid optics of prior art devices necessary for imaging conventional fluorophores preclude maneuvering within in small, minimally invasive tumor cavities, and imaging the entire surface area with high sensitivity (<200 cells) as well as accessing lymph node basins. Standard postoperative pathologic evaluation of excised tumor specimens can result in sampling error, challenges with co-registration back to the tumor cavity, and can leave lymph node involvement unchecked.

Recognizing the importance of integrating molecular imaging with cancer surgery and radiation across cancer types, such as in the treatment of breast and prostate cancer, the disclosed system 10 for molecular imaging that removes the restrictions of current bulky imagers, enabling seamless molecular imaging in virtually any tissue contacted by a surgical instrument such as a scalpel or glove.

In various implementations, the disclosed imaging system 10 and associated devices and methods are used to image tissue through the use of optical nanoparticles such as upconverting nanoparticles. In various implementations, the system 10 utilizes different times and/or wavelengths to image. That is, in certain implementations, the system illuminates the tissue at a first wavelength and images or absorbs emitted light at a second wavelength. Further, in certain implementations, the system 10 is used to illuminate the tissue at a first time and image it at a second time, such as after the illumination has ceased. This is made possible through the use of optical nanoparticles that emit or luminesce absorbed light at a second wavelength (higher or lower than the first wavelength) and/or optical nanoparticles that emit or luminesce after illumination has ceased, in certain implementations for 1 or more microseconds longer. In further implementations, the system 10 can be configured to operate in a patterned or time-resolved matter, as described herein. Other optical nanoparticles can be used that have the properties of upconversion and long luminescent lifetimes (greater than one microsecond). These can be of a variety of compositions, including modifications of the outer shell coating, polymer wrapping and surface functionalization (to allow for attachment to targeted molecules such as proteins, small molecules and antibodies, or derivatives thereof).

Figure 1B:
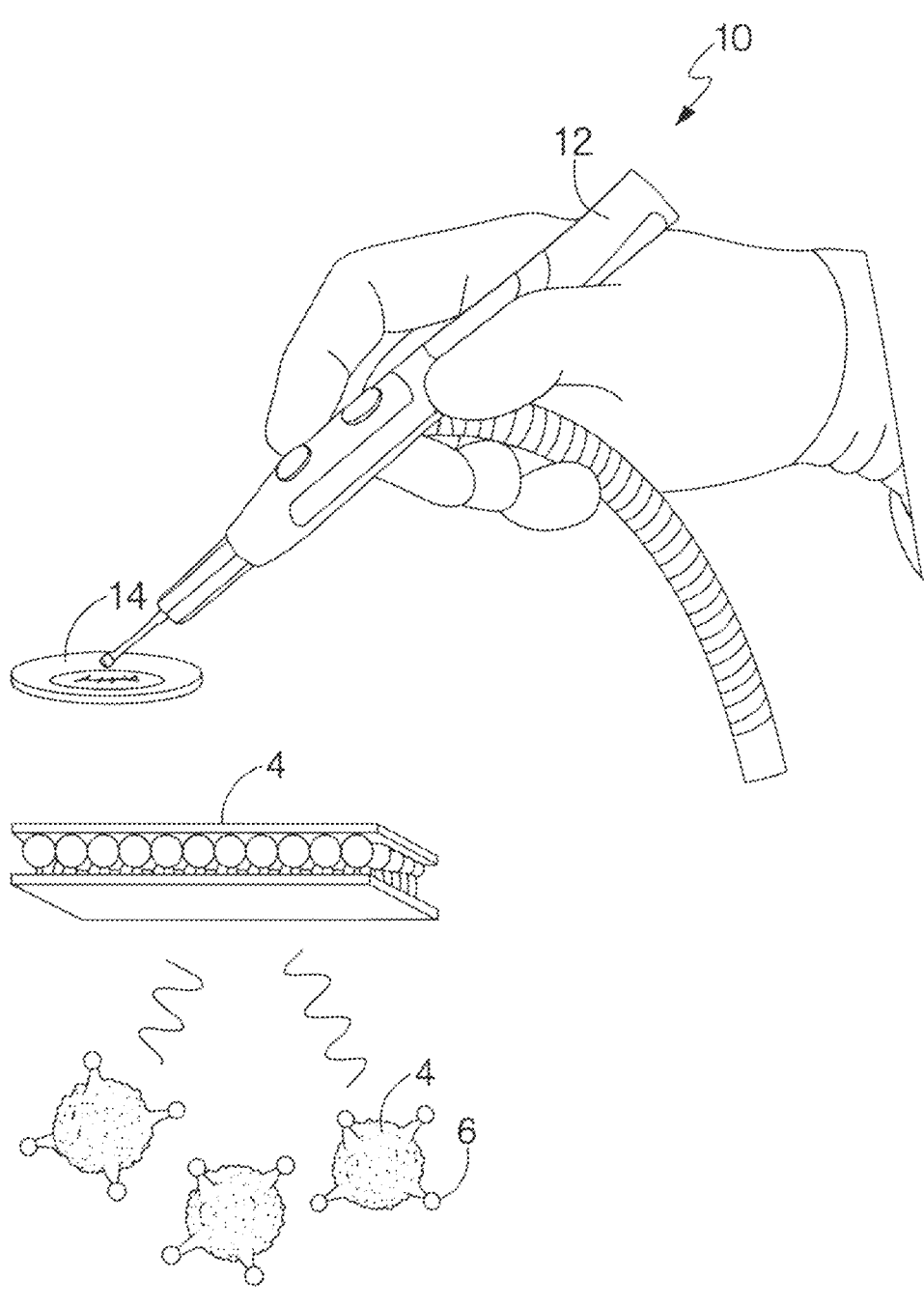
Figure 1C:
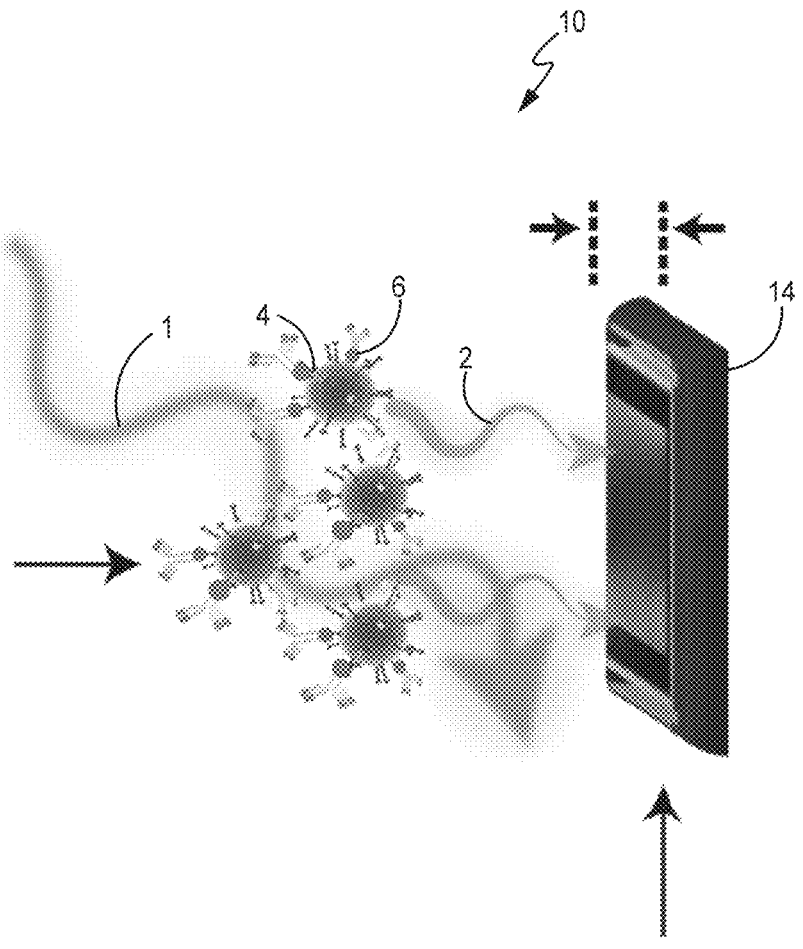
Figure 1D:
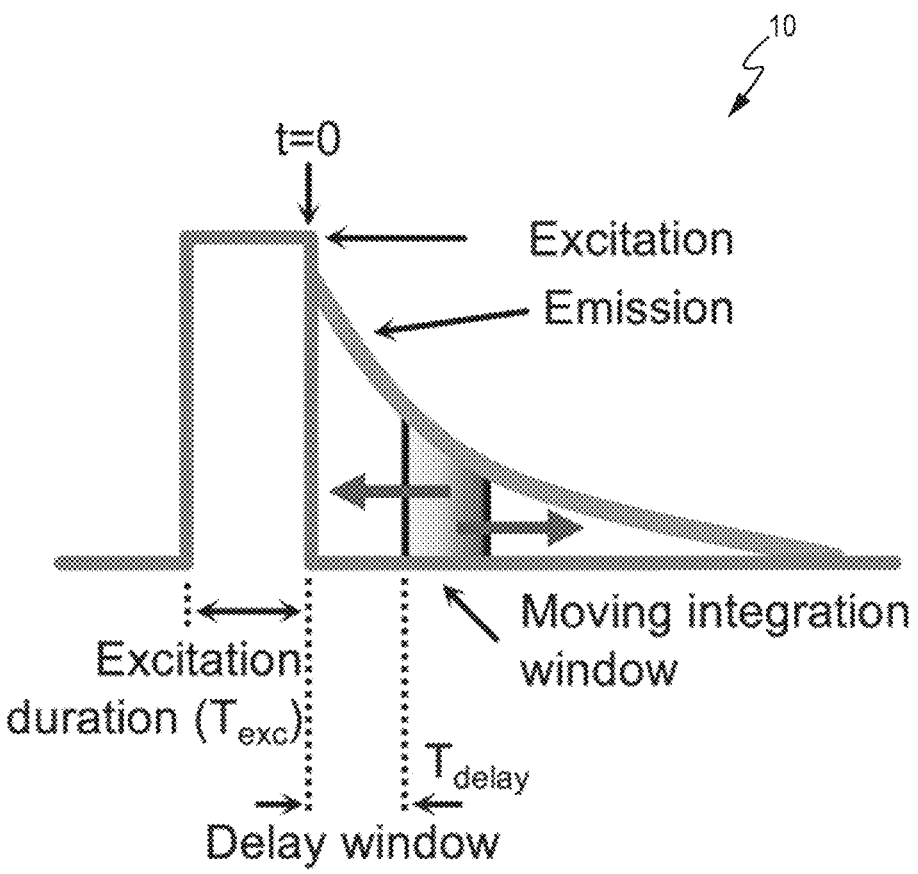
Figure 1E:
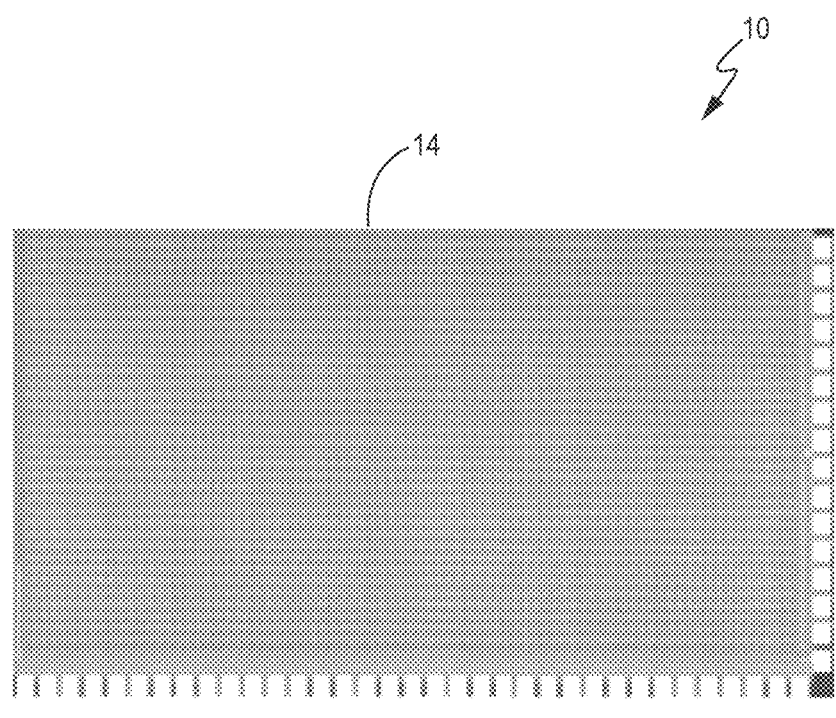
Figure 1F:
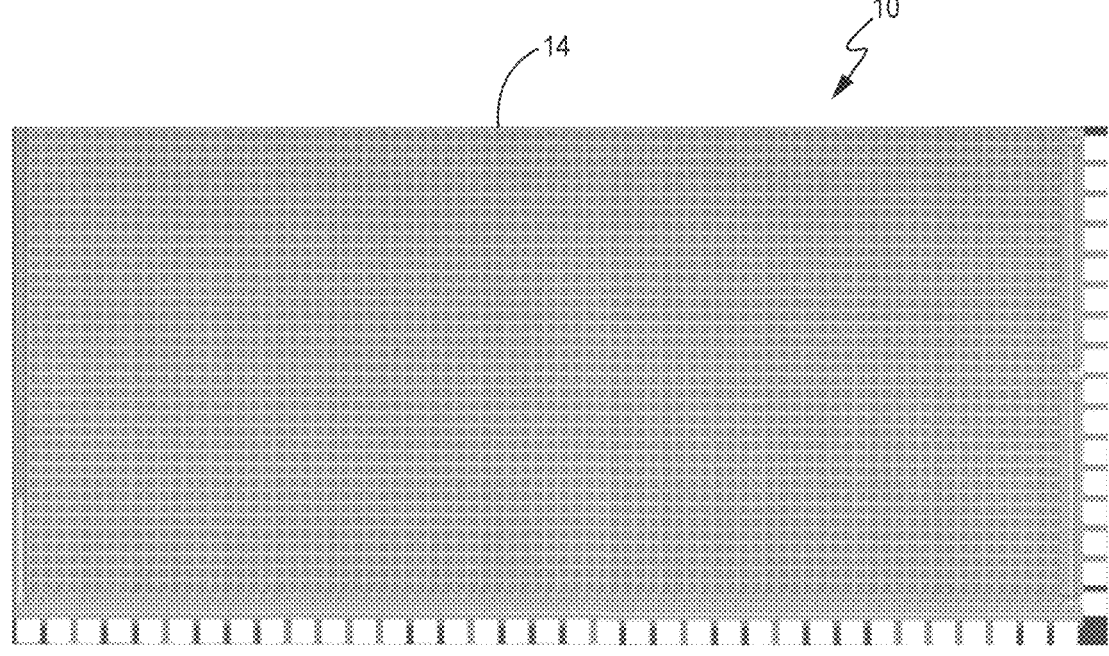
Figure 1G:
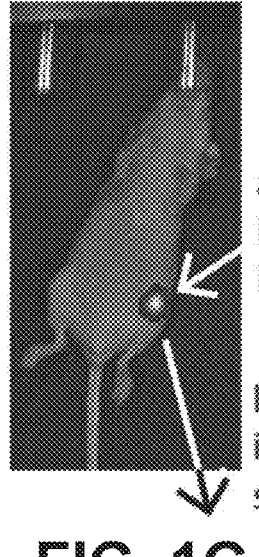

Turning to the drawings in greater detail, FIGS. 1A-H depict an overview and various aspects of the system 10 and associated methods and devices, according to certain implementations. As shown in FIGS. 1A-1B, in certain implementations, the system 10 comprises an imager 14 mounted on a surgical device 12, certain non-limiting examples being a glove 12 or scalpel 12, though it is readily appreciated that many other alternative devices are of course possible, such as mounting the imager 14 on a standalone probe or biopsy needle, or integrating the imager 14 into surgical robotic tools and the like. In these implementations, the imager 14 is constructed and arranged to detect signals 2 emitted from tissue 4 by upconverting nanoparticles (UCNPs) 6. Various implementations of the system 10 for the direct integration of an imager 14 with surgical tools 12 are outlined here.

According to various implementations, the imager 14 is a high-speed integrated circuit (IC) imaging array configured to be used with biocompatible alloyed UCNPs 2-3 orders of magnitude brighter than conventional UCNPs to image disease tissue 4. Such use of UCNPs 6 are able to make use of both an extended luminescence window—a long optical delay—and the characteristic of the UNCPs flourescence to higher energies to avoid the need for the lenses and/or filters of prior art imaging devices, see, for example.

As such, the present system 10 and associated devices and methods relieve the cumbersome optical requirements imposed by organic fluorophores in favor of an optics-free microfabricated, scalable, time-resolved contact imaging (TRI) array imager 14. The system 10 thereby enables molecularly-guided resection and targeted irradiation of advanced cancers far more precisely than current empiric-based strategies, eliminating the 30% of cancer surgeries that are unsuccessful due to the inability to visualize microscopic disease, and transforming postoperative radiation therapy (PORT) planning with precision localization of tumor cells.

By taking advantage of imaging from within the body, microns to millimeters away from the subject tissue, the various implementations of the system 10 achieve single-cell intraoperative imaging throughout the surgical bed by dispensing with limitations of organic fluorophores in favor of UCNPs, which, as shown for example in FIGS. 1A-E, can be conjugated to antibodies (UCNP-Ab) targeted to cancer-specific markers.

Conceptually, using only a single preoperative injection of UCNPs-Ab, tumor cells are precisely labeled in vivo. Made possible by highly-efficient UCNPs 6, which allow for 2-photon imaging at fluences compatible with hand-held in vivo applications, optics are eliminated by shifting the requirement for color imaging to the time domain, well suited for high-speed electronics using the unique UCNP properties of near-infrared absorbance and upconversion to image tissue 4 labeled UCNPs 6 such that the emitted light 2 is at a higher energy than the absorbed light 1.

Figure 1H:
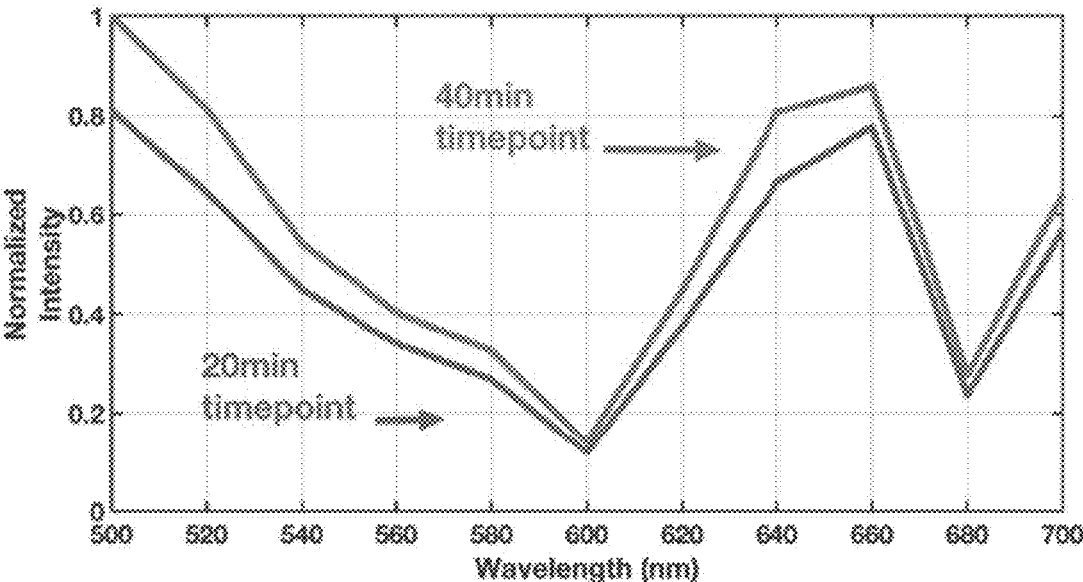
Figure 2:
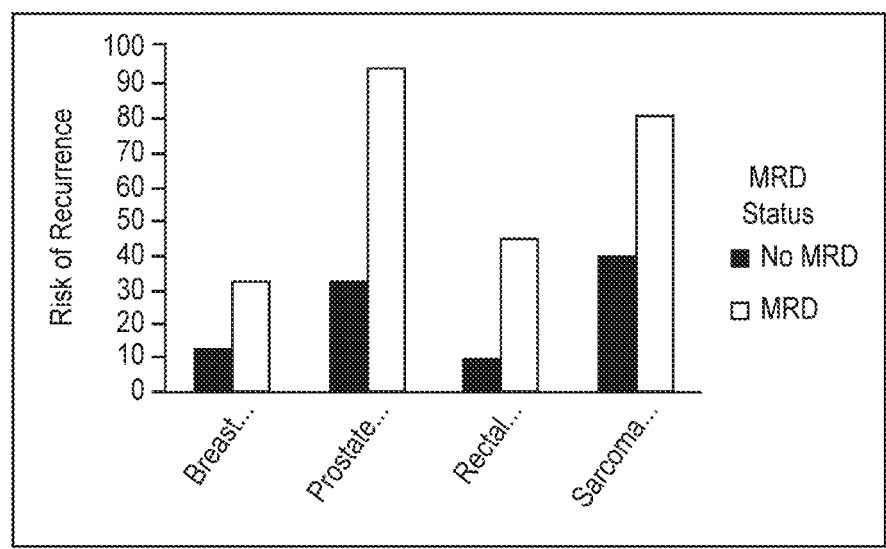
FIG. 2 is a bar graph depicting the risk of recurrence with MRD.

As shown in FIG. 1H, the near-infrared (about 980 nm) absorbance allows simple through-illumination of silicon (transparent at these wavelengths), deep into tissue, while the upconversion—a uniquely efficient ability to absorb photons in the near-infrared range (NIR) and emit light 2 at higher energies—transforms the emitted signal into an easily imaged, visible photon devoid of background and autofluorescence.

Unfortunately, no clinical imaging methods are capable of detecting microscopic disease intraoperatively; conventional imagers such as CT, MRI and PET are limited to a resolution of ~1 cm$^3$ or 10$^9$ cells, orders of magnitude above the ~200-cell threshold needed to image foci of MRD. The limited ability to identify microscopic tumor foci stems from both the imager's distance from the tumor cells, and a lack of definitive molecular identification, instead relying on inferred characteristics such as size and contrast enhancement. Strategies relying on cell morphology such as touch-prep or frozen section require an on-site pathologist and are complicated by the fatty nature of breast tissue, limiting their utilization.

Intraoperative fluorescent imaging. The self-limiting depth penetration of light reduces background while conveying useful information about the tissue surface and several millimeters below, ideal for tumor margin and lymph node imaging. Using targeted molecular agents, multiple animal studies demonstrate tumor labeling in vivo with fluorescently-labeled systemically injected antibody. Recent clinical trials employ this strategy to label tumor cells and guide resection intraoperatively, spanning ovarian, pancreatic, esophageal (NCT02129933) and breast (NCT01508572) cancers. Imaging agents targeting more general markers of tumor, such as matrix metalloproteinases (MMP), are in clinical trials, expanding applicability of this platform to a wide range of cancers. However, conventional organic fluorophores drive the need for bulky, rigid optics, precluding effective intraoperative imaging.

With an absorption cross section of approximately 10$^{-16}$ cm$^2$, quantum yield of ~10%, and Stokes shift of only ~50 nm, fluorescence imaging requires dual optical paths, a high performance optical filter, and focusing optics. Current intraoperative fluorescent imagers, are largely based on a similar principle of placing a large microscope above the tumor bed and are inadequate for two key reasons: (1) they are restricted to line of sight only, as rigid optics are required for fluorescent imaging (optical paths for excitation and emission light, focusing objectives), missing the majority of the tumor cavity surface; and (2) They image far from the tumor bed, restricted by the size of optics to outside the tumor cavity, reducing resolution and sensitivity as light diverges over the distance squared. Scaling current fluorescent microscopes to mm-scale encounters fundamental limitations as fabricating optics at the micro-scale introduces significant aberration due to imperfections, and imagers are still several centimeters in length. Light-sheet microscopy requires external optics, precluding use in the tumor bed. Fiber optic approaches lack the maneuverability necessary for small lumpectomy cavities, facing a fundamental tradeoff between flexibility and fiber diameter, significantly limiting the area imaged for a flexible fiber.

Given that imaging devices themselves remain the limiting factor in translating the high-contrast molecular imaging of the pathology lab into the operating room to identify MRD anywhere in the surgical field, the various implementations of the system 10 dispense with optics altogether, embedding a photosensitive imaging skin into any surgical device. By placing the imager skin directly onto the tissue surface—increasing sensitivity via micron proximity while being small enough to manipulate within the cavity—the system 10 allows the user to thoroughly image the entire surface with high sensitivity.

Figure 3A:
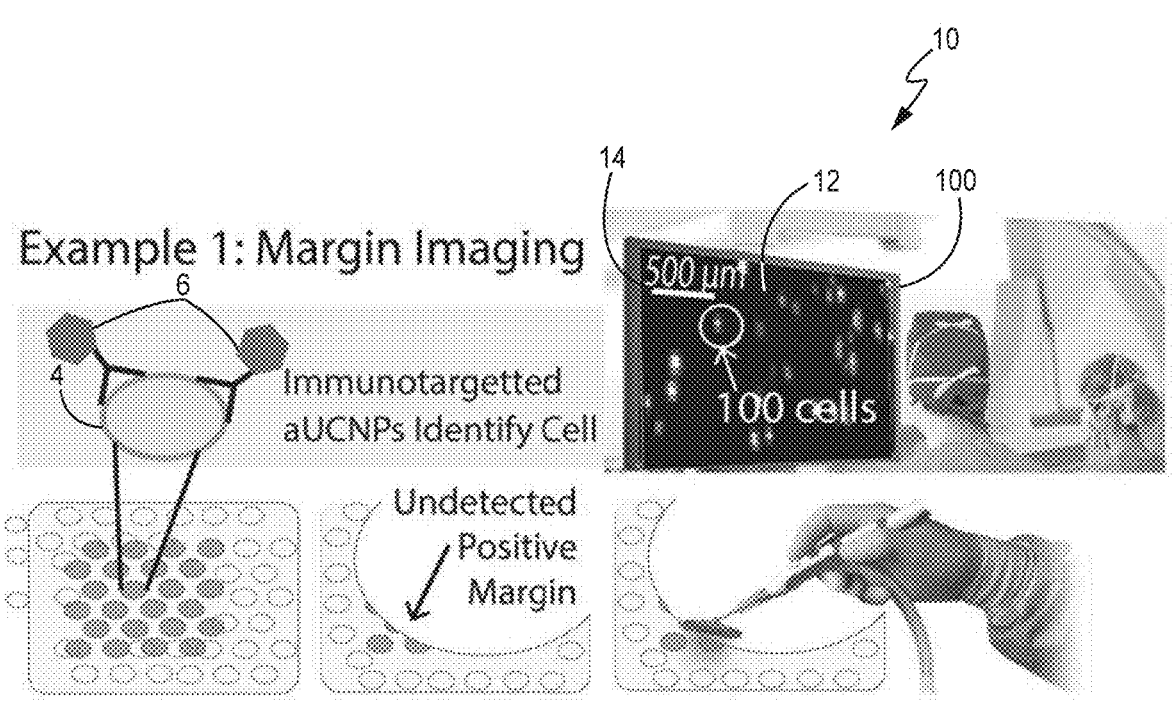
FIG. 3 depicts a workflow wherein nanoparticles with unique optical properties (including long luminescent lifetimes, >10 microseconds, and up conversion, an example of which are upconverting nanoparticles or UCNPs) are injected intratumorally or systemically, labeling tumor cells in vivo. These nanoparticles can be conjugated to targeted molecules, such as small molecules and antibodies (referred to as immunotargetted UCNPs). Tools with the molecular imager embedded on their surface then resect (Example 1) or are inserted into tissue (Example 2), such as in a lumpectomy/prostatectomy or biopsy, respectively. The real-time (<0.01 s) images are projected onto a monitor and automated image recognition software identifies and quantifies the cells seen.
Figure 3B:
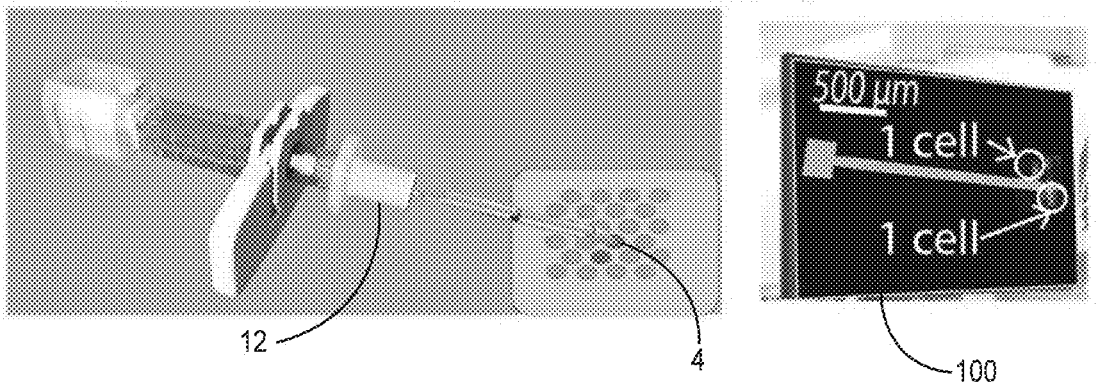
Figures 4A, 4B, 4C, 4D:
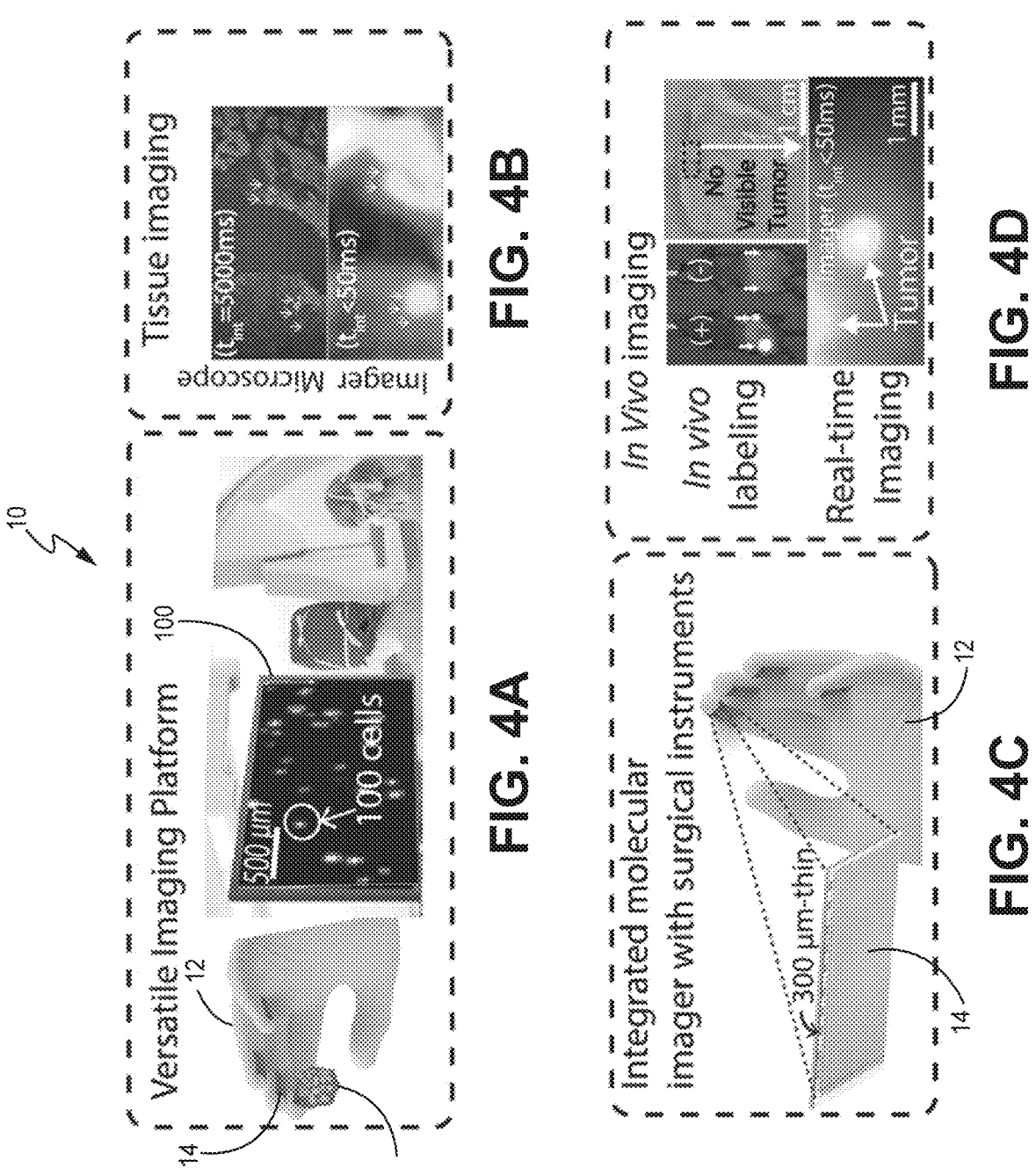
FIG. 4 is an overview of integrated imaging of single cancer cells with an ultrathin imaging chip embedded in surgical instruments.

To image single-cells directly within tissue, the various implementations of the system 10 represent a new imaging technology, that directly integrates into an ultra-thin, planar form-factor, that is embedded directly on surgical instrumentation, transforming the tool itself into a single-cell molecular imager (As shown in FIG. 1 and FIGS. 3-4) to guide precision cancer surgeries and biopsies, or any other invasive procedure. That is, FIGS. 3A-3B depict system 10 workflow according to two examples wherein immunotargeted aUCNPs 6 are injected intratumorally or systemically, labeling tumor cells in vivo. Instruments 12 with the molecular imager 14 embedded on their surface then resect (Example 1) or are inserted into tissue (Example 2), such as in a lumpectomy/prostatectomy or biopsy, respectively. The real-time (<0.01 s) images are projected onto a monitor 100 and automated image recognition software identifies and quantifies the cells seen, as would be readily understood.

FIG. 4A-4D depict a further views of integrated imaging of single cancer cells with an ultrathin imaging chip 14 embedded in surgical instruments 12, according to certain implementations of the system 10 showing the tissue and in vivo imaging of the labeling.

FIGS. 5A-5D are an overview of the system 10 according to certain implementations where the system 10 is upconverting and imaging nanoparticle. FIG. 5A shows the absorption, transfer, and emission in Yb3+/Er3+-based aUCNPs following either NIR-I (980 nm) or NIR-II (1550 nm) excitation. FIG. 5B depicts an imaging platform directly integrated onto surfaces, such surgical glove. FIG. 5C is a diagram of the time-resolved image acquisition configuration of the system 10, where Texc is pulse excitation time, Tint is emission signal integration time and Tdelay is time gating delay. FIG. 5C shows that angle-selective gratings can be used to achieve lensless image acquisition and block obliquely incident background light in certain implementations.

Figure 6:
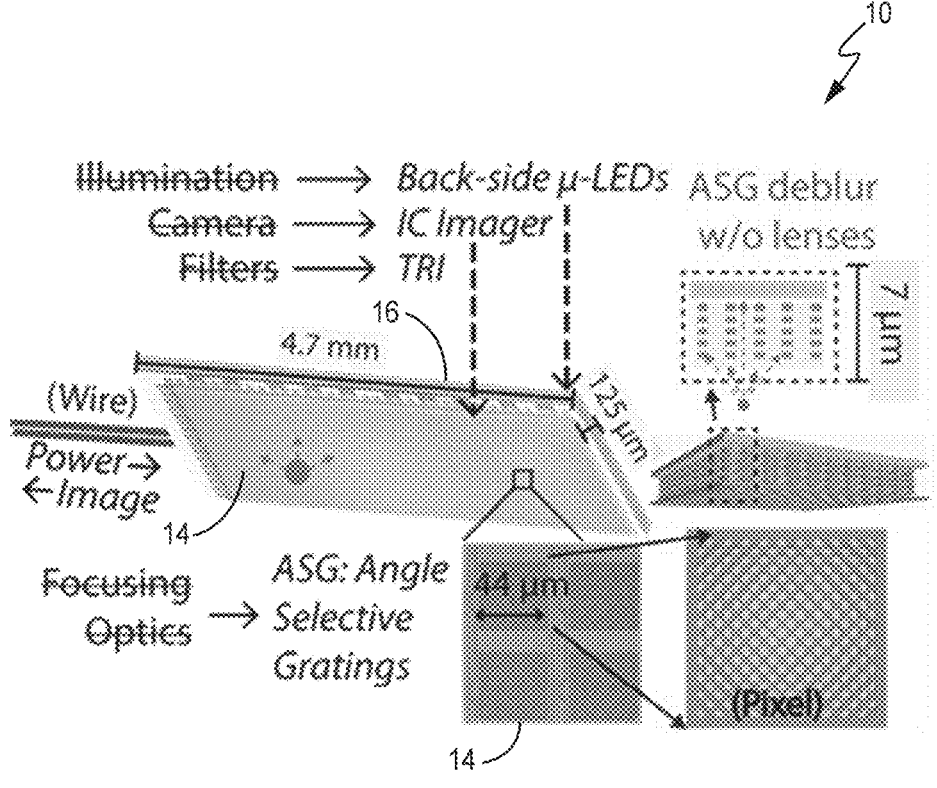
FIG. 6 depicts a view of an imager chip, according to one implementation. where each component of a conventional fluorescence microscope is transformed into microfabricated planar layer, or eliminated altogether. The prototype integrated circuit imaging chip alone is then capable of molecular imaging of cells labeled with aUCNPs.
Figure 7:
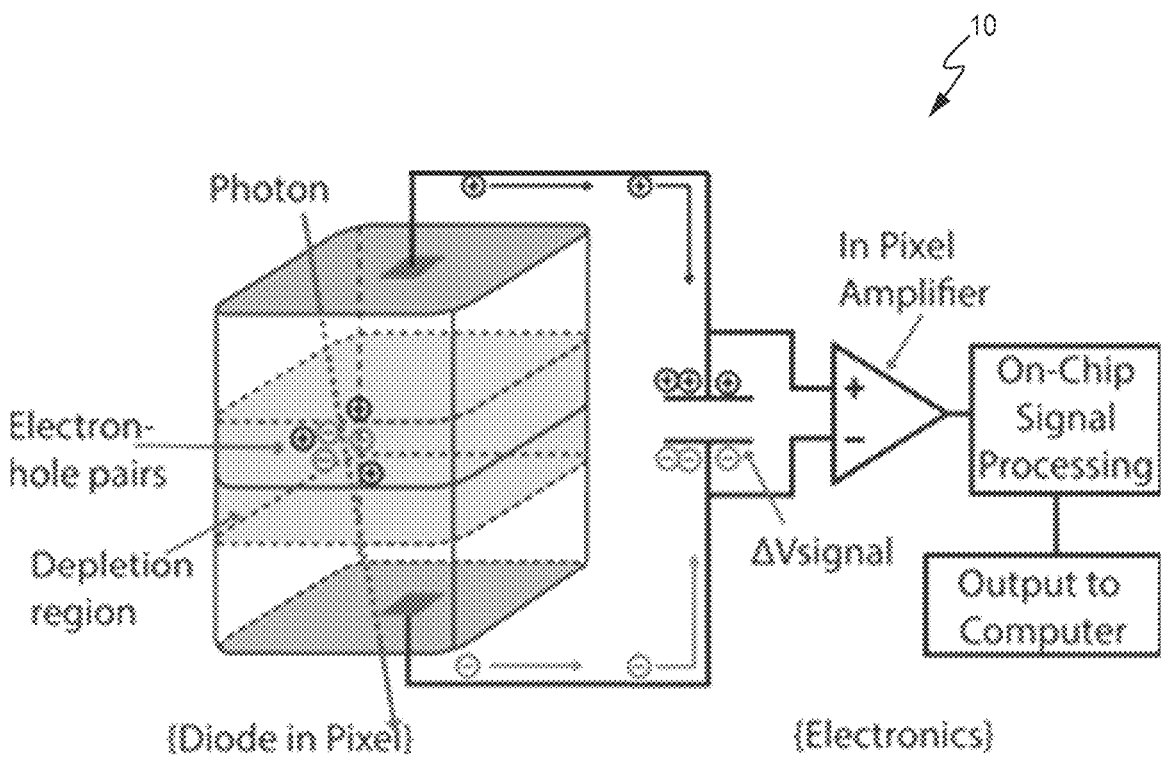
FIG. 7 is a photodiode pixel level photodiode and circuitry convert photons to electronic signals.

FIG. 6 depicts an imager chip 14 according to certain implementations of the system 10. It is appreciated that each component of a conventional fluorescence microscope (such as illumination, camera and filters) is transformed into microfabricated planar layer on the IC 14, or eliminated altogether. That is, the imaging chip 14 of FIG. 6 is configured for time-resolved imaging (TRI) and comprises a backside illumination source 16 such as a μLED array. Further, in lieu of focusing optics, the integrated circuit imaging chip 14 alone is then capable of molecular imaging of cells labeled with aUCNPs. FIG. 7 is a pixel-level schematic showing a photodiode and circuitry convert photons to electronic signals The various implementations of the system 10 introduce a fully integrated molecular imaging system, consisting of an optical label (for example, UCNPs) and a custom optics-free, high-sensitivity time-resolved integrated circuit. Enabled by the unique optical properties of UCNPs and similar particles, the various implementations of the system 10 eliminate or miniaturize each component of a conventional fluorescence microscope, resulting in an ultra-thin planar, imaging surface (See, e.g., FIGS. 1 and 4A-5D). The surface can have thin flexible wires to connect it to an external computer and monitor for data processing and visualization.

Figure 22:
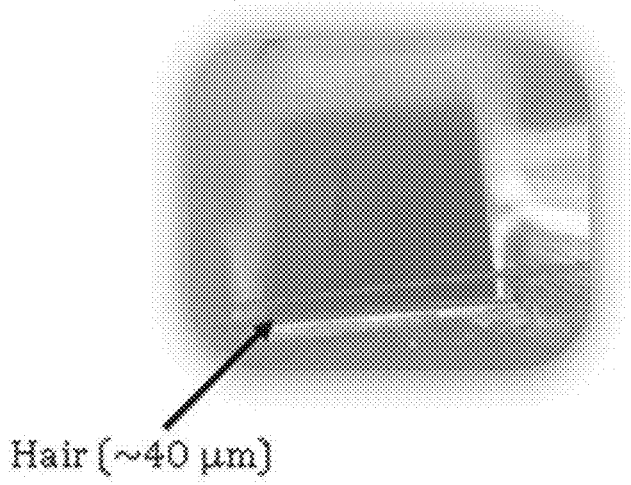
FIG. 22 shows an imager thinned to 25 microns and shown in comparison to a human hair.

Our key innovation is the synergistic integration of a novel molecular, <1 mm thin (and can be reduced to ≤25 microns thin (see below at FIG. 22), imaging skin made from integrated circuit technology and UCNPs, embedded on the surface of any surgical tool, transforming the tool itself into a molecular imager (shown for example in FIG. 1).

In certain aspects, the system 10 comprises an imager 14 having a highly sensitive imaging array in integrated circuit technology, turning the camera into a single chip. The imaging chip itself can be thinned to <25 μm and scaled to cm$^2$ dimensions, realizing a molecular imaging skin.

In certain aspects, the system 10 utilizes the long luminescent decay times of specific optical labels (such as UCNPs 6) to shift the cumbersome requirements of color (fluorescence) imaging into the time domain, synergistic with modern high-speed integrated circuits, eliminating the need for optical filters.

Optical filters are eliminated using time-resolved imaging: alternating pulses of illumination light and imaging only the decaying fluorescent signal emission, when the illumination light is off (FIG. 7B). This requires a long-luminescent lifetime optical particle.

The various implementations of the system 10 eliminate lenses using micron proximity to tissue and on-pixel angle selective gratings for deblurring.

Sensitivity is enhanced by proximity, gathering light before it divides, and low-noise circuit design.

Spatial resolution is achieved without lenses through micron-proximity to tissue, integration of on-chip angle selective gratings (7 μm tall structures integrated directly on photodiodes) and a high pixel density.

The various implementations of the system 10 eliminate conventional illumination sources and optical light guides through direct integration of light sources (for example LEDs or laser diodes) to the backside of the imaging chip, shining NIR light directly through silicon (transparent at these wavelengths) and deep into tissue.

Through-illumination solves challenges in illuminating tissue beneath the opaque contact imager: By fixing light sources (such as light emitting diodes or laser diodes, or fiber optics) that emit infrared light at a wavelength longer than about 1000 nm, directly to the back of the silicon-based imager, which is transparent at these wavelengths, tissue is directly illuminated through the chip itself. This eliminates both relatively inflexible fiber optics and inefficient side-coupled illumination, which requires an optical particle with IR absolution greater than about 1000 nm. However, because Stokes shifted light will be even a longer wavelength and therefore pass through silicon-based photodiodes, we require visible to near IR light to be emitted from the tissue being imaged, which requires an optical particle capable of up conversion (bound to the tissue). Up conversion also eliminates autofluorescence since no naturally occurring tissues have this property.

Conversion of light to an electronic image at the sensing point obviates fiber optics without loss of sensitivity. As such, inflexible optics fibers are eliminated by converting the optical signal to an electrical one at the tissue surface using integrated circuit-based contact imager.

Integration of silicon nanophotonics for a monolithically integrated sensor. Integration of on chip illumination using silicon nanophotonics allows light to be routed on chip. This allows light to be pattered at the pixel level. The resulting pattered illumination can increase the spatial resolution beyond that of the imager alone.

Depth imaging using ratio metric imaging. By illuminating nanoparticles that can absorb at two different wavelengths, and each wavelength has different absorbances in tissue, the relative intensities of the two images can provide information about tumor depth. In one application for UCNPs, this works because illumination light at 980 nm will pass to a depth "d" with a different, intensity (and loss) than illumination light at 1550 nm. Using this principle we can derive the dimension information about the distribution of nanoparticles (and the cells they label or identify) below the tissue surface. Calibration of ratiometric imaging can be done on tissue phantoms prior to use for imaging. Ratiometric imaging can be used with any of the illumination strategies outlined herein.

In implementations where LEDs or laser diodes are used, two or more wavelengths can be used and alternated. In implementations where fiber optics are used a single fiber optic can be used and two different light sources can be alternated sequentially. Similarly, a fiber optic bundle can be used and different wavelengths of light can be channeled through different individual fibers within the bundle and illuminated sequentially. Two or more wavelengths can be used, such as wavelengths differing by about 50 nm or more. Here, examples of 980 nm and 1550 nm were used, but any wavelengths can be used that are absorbed by a nanoparticle and cause optical emission by that nanoparticle.

Optical labels. Conventional fluorophores have extremely fast time constants (nano second)—making time—resolved imaging challenging for an array-based sensor, required for spatial resolution and rapid imaging over a large surface area, where thousands of pixels must function simultaneously. Few fluorophores absorb in the infrared, and two photon processes necessary for upconversion are highly inefficient, requiring power levels incompatible with in vivo use.

It is appreciated that any organic or inorganic optical label that can: upconvert with a lifetime of greater than about 1 ms lifetime is compatible with this system. That is, any label that can upconvert by emitting at a higher energy (shorter wavelength) after absorbing lower energy (longer wavelength) photons for more than about 1 ms is contemplated by the system.

One such optical label are upconverting nanoparticles. Examples include upconverting nanoparticles (UCNPs) and UCNPs with shells, which allow longer radiative lifetimes. References include and commercial products such as Creative Diagnostics (DNL-H011 DiagNano™ PEG-NH2 Upconverting Nanoparticles, 545 nm/660 nm, DNL-H003 DiagNano™ PEG-COOH Upconverting Nanoparticles, 545 nm/660 nm). Any other particle or optical label that fulfills these requirements can also be used.

UCNPs simultaneously address both these challenges, enabling a first-in-class imager with their uniquely long luminescent lifetimes (>100 μs), IR absorption, and up-conversion, allowing development of an array-based time-resolved imaging platform using only CMOS (complementary metal oxide semiconductor)—enabling a first-in-class scalable, ultrathin molecular imaging array. Substrates for the imaging chips and photosensors include silicon, germanium, gallium phosphide (GaP), indium gallium arsenide (InGaAs), indium arsenide antimonide, lead sulfide, diamond-based photodetectors and mercury cadmium telluride photodiodes and other similar substrates understood and appreciated in the art. Existing methodologies allow for protein conjugation to inorganic nanoparticles, including UCNPs. Nanoparticles with core-shells have longer lifetimes, and techniques in coating including new materials in shells around the core, can increase optical lifetimes.

The disclosed Examples demonstrate the feasibility of time-resolved imaging of UCNPs with the imaging array. The UCNP decay time constant is sufficiently long for array-based time-resolved IC imaging, (2) spatial feature recognition drawing from the previous demonstration in fluorescent contact imagers using angle selective gratings, and (3) live animal imaging of UCNPs linking in vivo biodistribution experiments with imager findings.

A custom ultra-thin high-sensitivity imager. Starting with a custom 2,880-pixel prototype image sensor, with a scalable architecture made from integrated circuit (IC) technology, the various implementations of the system 10 design the sensor to be an ultra-sensitive detector of photons, such as is shown in FIG. 6. Each 44 μm pixel consists of a photo-diode, converting an incident photon into an electronic signal, as shown in FIG. 7, amplified by in-pixel circuitry.

As shown in the incorporated references, ultra-rapid (<0.1 s) fluorescence imaging of tissue and cellular foci (down to 20 cells) using a custom, lensless integrated circuit imaging platform is possible. the demonstrated low noise design approaches the shot-noise limit, representing the fundamental limits of optical detection. This effectively replaces a conventional camera with a single "chip"—readily thinned to just 25 μm microns, as is demonstrated in FIG. 17B. However, fluorescence imaging requires both optical filters and fiber optics or waveguides to guide light into tissue, hindering direct integration into surgical instruments. Furthermore, background tissue autofluorescence and incomplete rejection of illumination light through the filter significantly limit sensitivity at the single-cell level. The various implementations of the system 10 overcome these limitations through the integration of optical nanoparticles, such as UCNPs, with dual properties of upconversion and long decay lifetimes.

Upconversion enables imaging without background. Since silicon is relatively transparent to 980 nm and 1550 nm—the two absorption peaks of the UCNPs—it cannot detect a conventionally Stokes shifted photon—which would be at a lower energy (longer wavelength) and even more challenging to detect. However, the various implementations of the system 10 take advantage of upconversion and easily capture the emitted photon of immunotargeted UCNPs bound to tumor cells in the visible spectrum, readily absorbed by silicon. Upconversion has another distinct advantage—no background tissue autofluorescence. Without background, the imager noise (and dark current) is designed to be below the intrinsic shot noise of the tumor signal, achieving single-cell detection.

Imaging within the optical window of tissue. It was proposed to use 980 nm illumination for in vivo imaging, as it falls within the optical window (low absorbance region) of tissue. However, given that 1550 nm has greater absorbance in tissue, it has the advantage of imaging closer to the tissue surface (reducing background from non-specific binding within the tissue), useful for sensitive margin imaging. Since UCNPs can absorb at both wavelengths, in the Examples described herein, implementations of the system 10 were used to sequentially image at 1550 nm and 980 nm, thereby imaging both at the surface and deeper into tissue, respectively.

Deriving depth imaging using combinations of 1550 nm and 980 nm illumination. The various implementations of the system 10 described herein are able to determine the relative depth of labeled cells by exploiting the dual optical absorption windows of UCNPs, which absorb light at both 1550 and 980 nm. Tissue, labeled cells (or any substance containing UCNPs) is illumination sequential with 1550 nm light and an image is taken, and then 980 nm light, and another image is taken. The relative intensities of these images, with the different depth penetration, absorption and scatter properties of the excitation light taken into account (as well as any shifts in emission spectrum with 1550 nm excitation versus 980 nm excitation), can be used to derive the location in tissue of the UCNPs.

Time resolved imaging (TRI) and the elimination of optical filters. The various implementations eliminate optical filters, required to remove the illumination light—which is many orders of magnitude stronger than the 2 or 3 photon, upconverted emission light. Conventional fluorescence imagers use specialized optical interference filters to reject excitation light by a factor of $10^6$ or more—which in turn require optics for precision alignment. Here, the various implementations of the system 10 eliminate the need for optical filters altogether by taking advantage of the long luminescent lifetimes (~100s of microseconds) to enable time-resolved imaging (TRI) (FIG. 5 Overview).

Long decay lifetimes enable time-resolved imaging in modern CMOS technologies, and alleviate the need for optical filters entirely. While time resolved imaging has been demonstrated with organic and protein fluorophores, their nanosecond radiative lifetimes make large, dense array based imaging impossible, as arrayed CMOS sensors cannot readily detect on timescales shorter than tens of microseconds. Although single photon avalanche diodes that require specialized fabrication processes have been demonstrated to operate at these timescales, they are challenging to fabricate in a high density, massively parallel array-based approach to enable large spatial coverage, high fill factor, and adequate spatial resolution necessary for efficient chip-based imaging. Consequently, a chip-based imager using time resolved imaging requires optical probes with microsecond lifetimes, such as upconverting nanoparticles. The long (>1 microsecond) decay lifetimes open the door to time-resolved imaging in an array-based CMOS imager.

Time resolved imaging (also called time-gated imaging). The various implementations of the system 10 illuminate with a pulse of light, transiently exciting the optical nanoparticles (e.g. UCNPs), and image within microseconds after the excitation light is turned off—completely eliminating background light, such as in FIG. 5. This process can be repeated, and images can be averaged together to improve image quality (signal to noise ratio or SNR). and sequential images can be averaged to improve image quality. The pulse of light can be any length of time that results in illumination and subsequent optical emission from the particle. This can be as short as 1 nanosecond, to as long as several seconds. In practicality, we select the pulse duration to be the duration that results in the maximal optical emission, which for the UCNPs tested here is approximately 1 millisecond. This can be customized for each nanoparticle. Pulse durations beyond that are not necessary. Shorter pulses (that achieve adequate optical emission from the nanoparticles) are advantageous because they reduce the total imaging time, and allow for either more rapid imaging, or more serial images to be taken and averaged, improving the image quality (SNR). After the illumination light pulse is off, the image is taken. The illumination light is off for the duration of the image. There is a small delay (Tdelay) between the illumination light being turned off and the image taken, and this can be adjusted. This delay is to allow any transients in the imager chip as a result of the illumination to decay. The image is taken with a set integration time. The image can be stored on chip, transmitted off chip, subjected to signal processing, digitized or any other standard process for an image.

The present imager according to certain implementations is a massively paralleled pixel array, captures the decaying, upconverted, emission with high spatial resolution. The relatively long UCNP lifetime allows integration times on the order of 100-1000 microseconds, which are achievable in modern CMOS processes.

The chip-based time-resolved imaging (also referred to as time-gated imaging) method of the current system 10 takes advantage of uniquely long emission lifetimes for select optical labels with one example being UCNPs. The long decay lifetimes alleviates the need for high performance frequency-selective (color) filters by separating the emission and excitation signals in the time domain rather than in frequency domain, a strategy that can be implemented in modern high-speed integrated circuit design. In a chip-based imager, the various implementations of the system 10 implement this by briefly pulsing the excitation light (for example, $T_{exc}$=5 ms duration although any excitation duration can be used sufficient to impart energy to the optical label) while the imaging pixels are not integrating. After the excitation light is turned off, the pixels are turned on, and integrate the emission signal from the UCNPs for 1 ms, as shown in FIG. 5. Since there is no background excitation light at this time, the need for an optical filter is eliminated. The illumination and signal acquisition scheme (FIG. 5C), where the excitation light source is pulsed for $T_{exc}$, and subsequently turned off, after which the emission signal from the UCNPs is acquired and integrated by the imager. Any interference and unwanted signal caused by the excitation light can be rejected by delaying (Tdelay) the integration window start point.

In order to determine whether an ASIC can image optical labels without the use of conventional focusing lenses and optical filters, the various implementations of the system 10 are designed and fabricated an imaging array capable of time resolved imaging, as shown in FIG. 5. Absent optics, the imaging chip can be easily thinned to just 25 microns and placed directly on tissue, increasing sensitivity through proximity—capturing light from optical labels before it diverges. The key to this platform is the transformation of molecular imaging from the color (frequency) domain to the time domain enabled by UCNPs. The various implementations of the system 10 accomplish this using synergistic design of modern integrated-circuits and upconverting nanoparticles. A key advantage of using CMOS-based imaging platform is the ability to integrate in-pixel electronics enabling signal processing directly on-chip, eliminating the need for optical lenses. This imager addresses both elimination of lenses and filters simultaneously, making it possible to obtain optical images with a much smaller form-factor.

Optical characterization. UCNPs emission and lifetimes were characterized as functions of illumination intensity, illumination pulse duration, each with either 980 or 1550 nm excitation. Vials of hydrophobic UNCPs dispersions in hexane (400 μL of the 0.68 μM) were placed above the imager array and excited with time-resolved collimated lasers. The beam was positioned 2 mm above the surface of the imager.

INSITE samples were excited with a 980-nm wavelength-stabilized, single-mode, fiber-coupled laser diode (Qphotonics QFBGLD-980-500) followed by an adjustable collimator (Thorlabs ZC618FC-B) set to a beam diameter of 1.27 mm; or a 1550-nm single-mode, fiber-coupled laser diode (Qphotonics QFLD-1550-1505) collimated by an aspheric collimator (Thorlabs CFS2-1550-APC) with a beam diameter of approximately 0.3 mm. Both lasers were driven by a temperature-controlled mount driver (Arroyo Instruments 6310 ComboSource).

Radiative lifetimes (τ) were modeled as a single exponential decay and were calculated by extracting decay profiles with a fixed moving integrating window ($T_{int}$). Assuming the dark current intensity ($i_d$) is constant over time, the various implementations of the system 10 derive the integrated pixel value $I_A(t)$ from the current density i(t):

$$i(t) = i_0 e^{\left(-\frac{t}{\tau}\right)} + i_d \rightarrow I_A(t) \equiv \int_t^{t+T_{int}} i(u)du$$

$$I_A(t) = \underbrace{i_0\tau\left[1 - e^{\left(-\frac{T_{int}}{\tau}\right)}\right]e^{\left(-\frac{t}{\tau}\right)}}_{I_{A_0}} + \underbrace{i_d T_{int}}_{I_d} = I_{A_0} e^{\left(-\frac{t}{\tau}\right)} + I_d$$

where τ and $I_D$ are the emission decay lifetime and dark current level in the pixel, respectively. Dark current level was subtracted from waveforms.

UCNP Sensitivity and Lifetime Measurements. To evaluate the sensitivity of the imaging platform for UCNPs the various implementations of the system 10 utilize and approach like that depicted in FIG. 8. the preliminary data demonstrates imaging UCNPs within the safe and allowable ASNI power limits—which reflect higher allowances for pulsed light (over continuous illumination). The various implementations of the system 10 have successfully imaged 0.68 μM UCNPs, over a volume of 3 μl (corresponding to $5\times10^5$ cells at $2\times10^7$ UCNPs/cell, equivalent to $1\times10^7$ cells at $10^6$ UCNPs/cell which is the expected number of aUNCPs per labelled cell) at 980 nm and 1550 nm. With millisecond pulses of 6 and 65 W/cm², respectively, at a relatively large 2 mm distance from the sensor surface, the various implementations of the system 10 detect UCNPs with an SNR of 26 dB and 22 dB at 980 and 1550 nm (as shown in FIGS. 9-10 and in Table 1).

Figure 8:
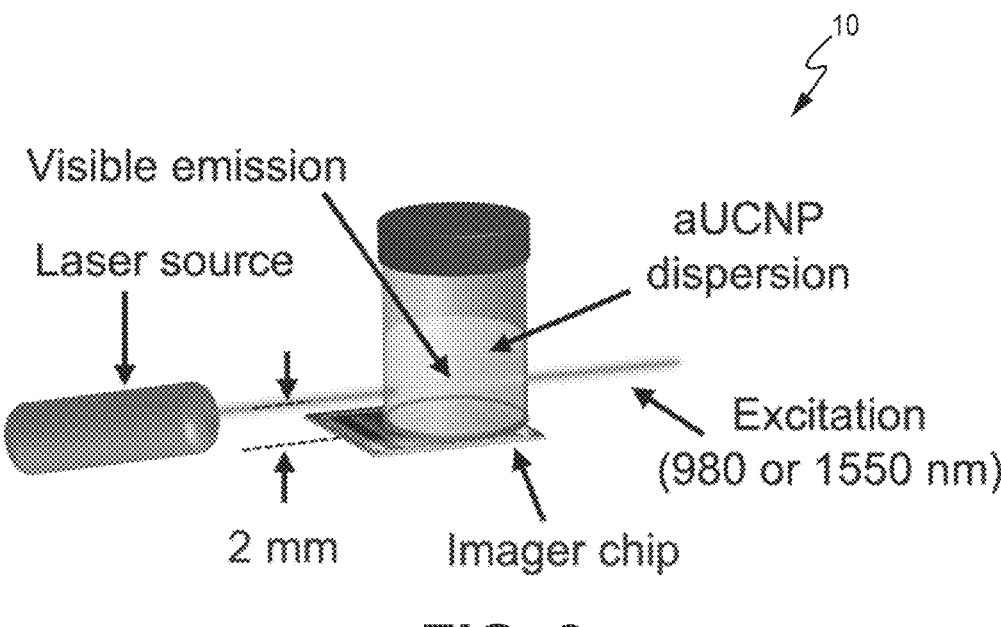
FIG. 8 depicts a setup INSITE configuration for imaging of aUCNP dispersions. Laser beam width is 300 μm
Figure 9:
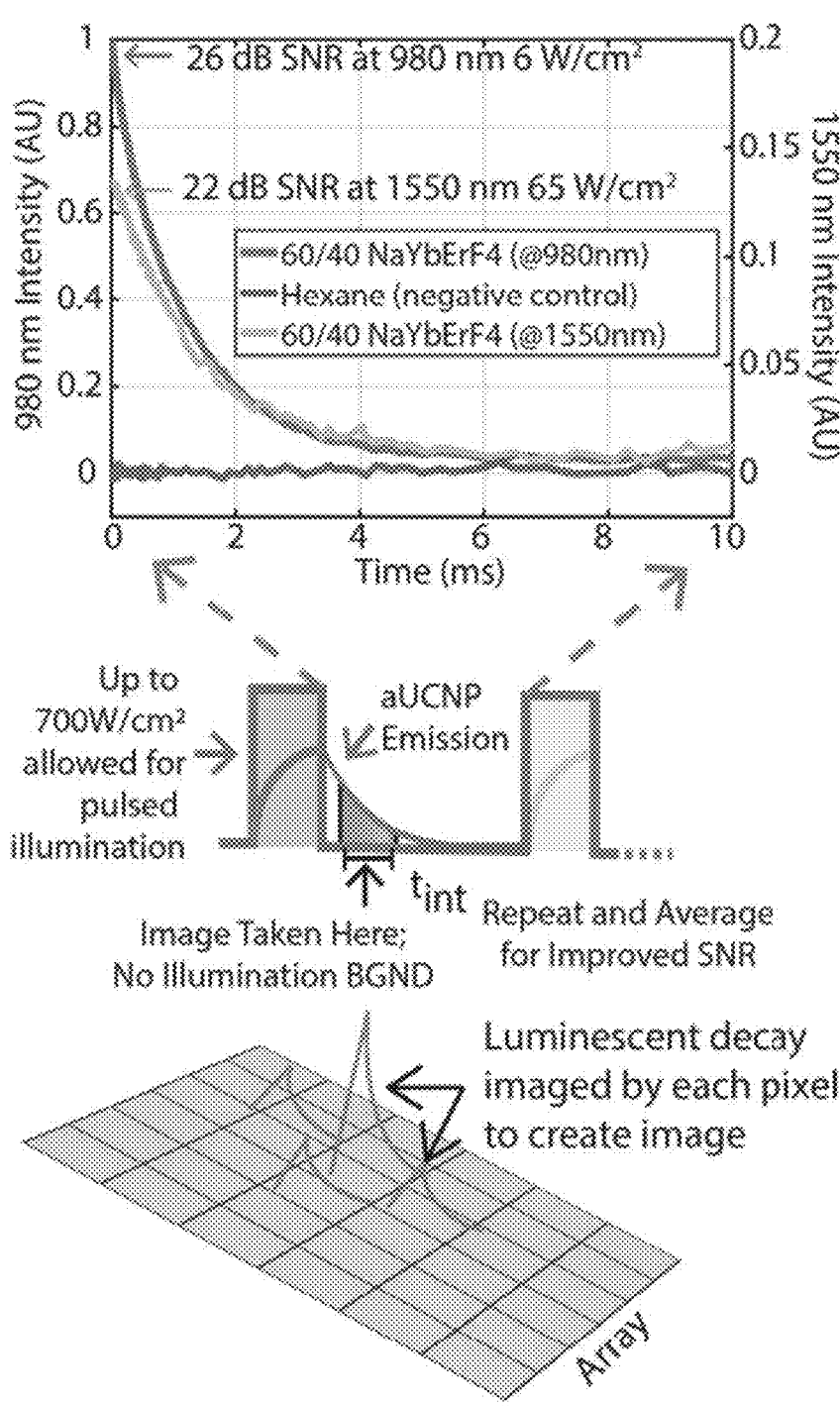
FIG. 9: Time-resolved Imaging (TRI) timing diagram, and measured 60/40 NaYbErF4 aUCNP time constant of using 25 μm thinned imager. (AU=arbitrary units)
Figure 10A:
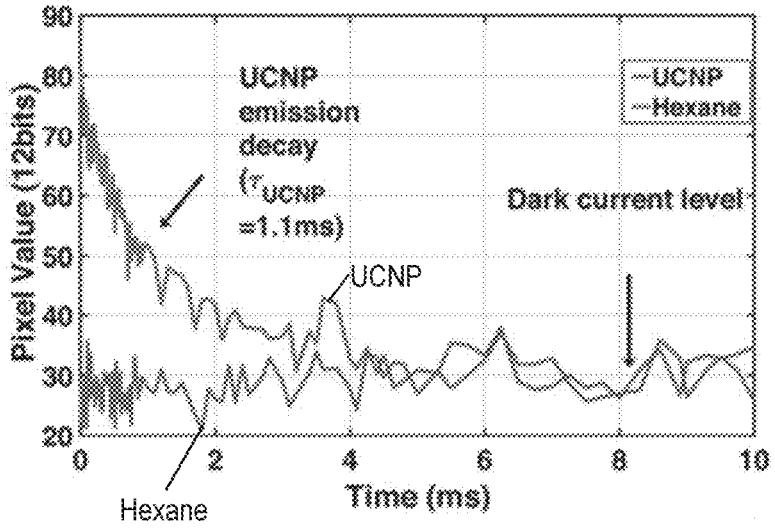
FIG. 10 shows UCNP emission measured with custom time-resolved imaging array. Emission decay (a) instantaneous and (b) integrated, showing background dark current. Emission vs illumination (c) power and (d) duration (peak 5 ms).
Figure 10B:
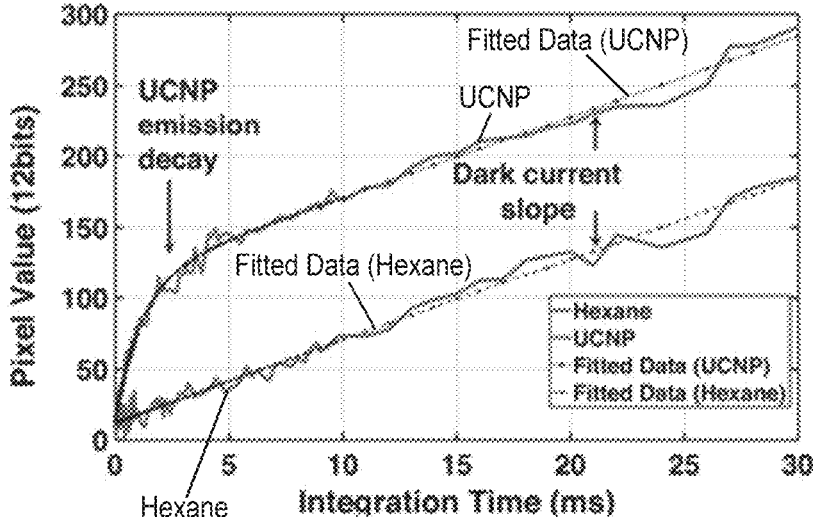
Figure 10C:
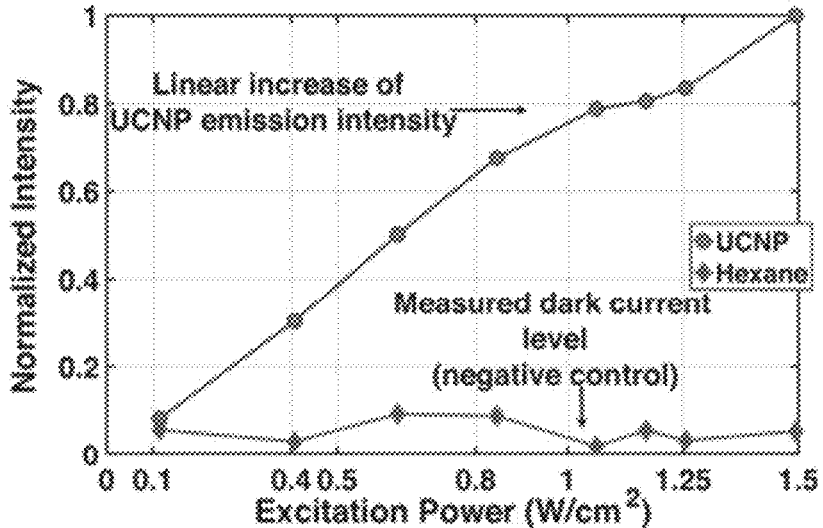
Figure 10D:
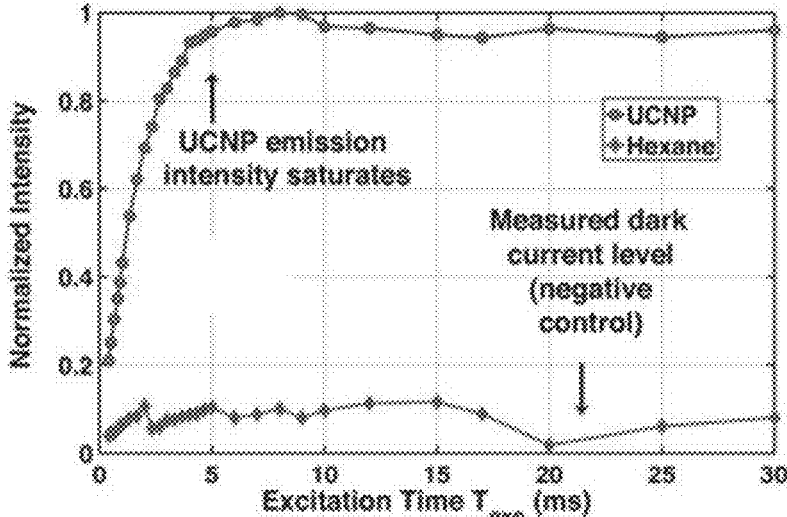

FIG. 8 shows the measured decay profile of the nanoparticles using the imager, thinned to just 25 μm, demonstrating an exponentially decaying photocurrent for the UCNP emission with a long lifetime of $t_{UCNP}$=1.1 ms, establishing feasibility of this approach with the prototype. Similarly, we have performed time-resolved imaging of several UCNP constructs with varying proportions of Yb and Er (at both 1550 nm and 980 nm (shown in FIG. 11E). 60/40 NaYbErF4 has the brightest emission and longest lifetimes at both 980 and 1550 nm, as shown in FIG. 11, leading us to select this construct for further development.

As shown in FIG. 10, UCNP imaging shows the measured decay profile of the nanoparticles using the imager (1 ms integration time), demonstrating an exponentially decaying photocurrent for the UCNP emission with a long lifetime of $t_{UCNP}$=1.1 ms. No background autofluorescence is visible due to the fact that their emission dissipates within pico to nanoseconds. The relative signal to background ratio (SBR) is measured by integrating the signal (serially increasing integration time from 1 to 30 ms), and optimal SBR of 3 is achieved after a 5 ms integration time, as shown in FIG. 10. As background is solely due to dark current, this will be reduced in subsequent designs.

Figures 11A, 11B:
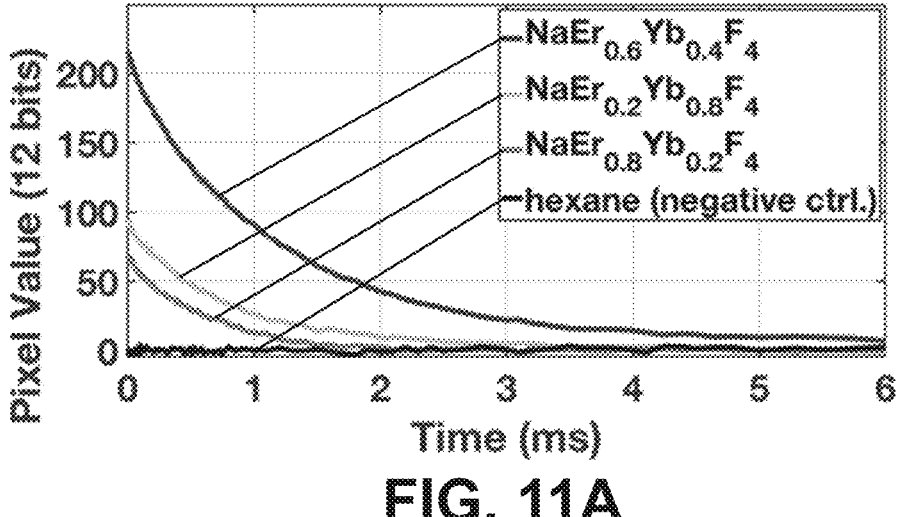
FIG. 11 depicts UCNP Decay versus Composition. Emission decays of UCNPs (Tint=1 ms, Texc=5 ms) as measured by pixel output at (A) 8 W/cm2 of 980 nm excitation, or (B) 60 W/cm2 of 1550 nm excitation. Tint is integration time; Texc is duration of excitation light pulse.
Figure 12:
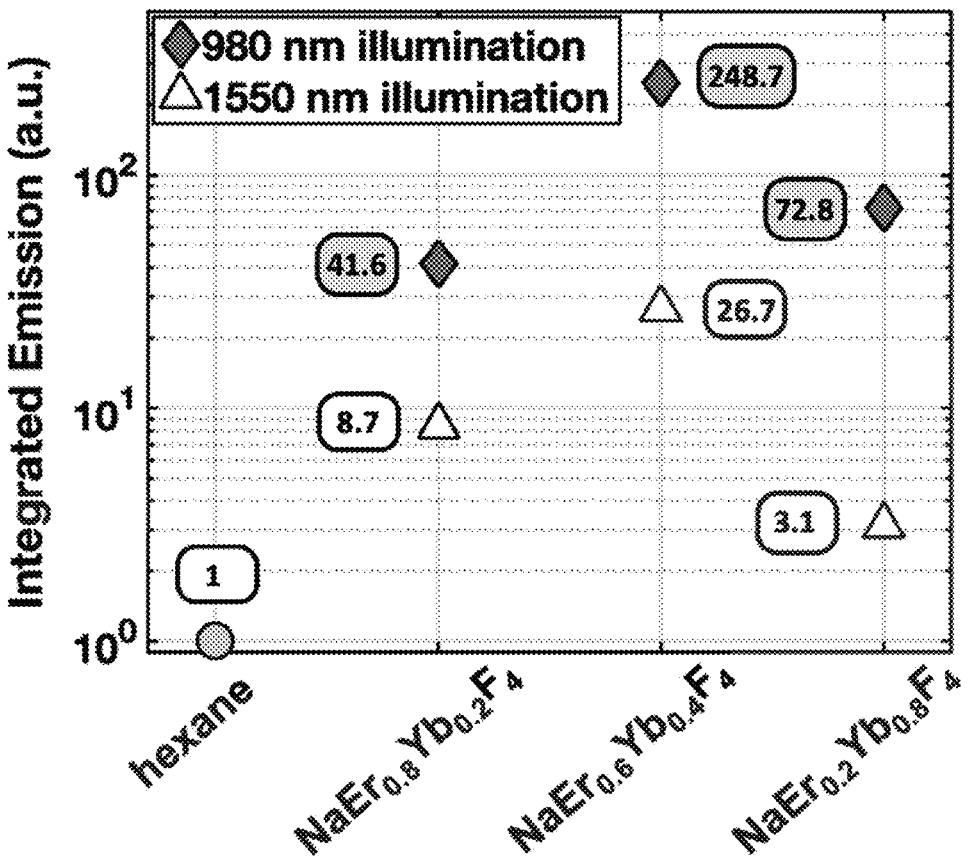
FIG. 12 shows integrated visible emission as a function of UCNP composition at either 980 and 1550 nm excitation, both with 8 W/cm2 excitation power density. Hexane blank is without UCNPs.

As further demonstration, the various implementations of the system 10 image a series of core/shell UCNPs with varying $Yb^{3+}$ and $Er^{3+}$ content to measure emission using either 980 nm or 1550 nm photoexcitation, as shown in FIG. 11. UCNP cores (8 nm) were synthesized with 20/80, 40/60, or 80/20 $Yb^{3+}/Er^{3+}$ ratios and overgrown with inert 4-nm shells. With these nanocrystals in the experimental setup, shown in FIG. 8, the initial emission intensity, A·, luminescence lifetime, τ, and total integrated emission count, A·τ, were measured at a given power density (8 W/cm² at either 980 and 1550 nm). Measured decays for varying UCNP compositions range from 600 μs to 1.3 ms at either 980 nm or 1550 nm excitation. These values are longer than measured or calculated, but consistent with UCNP power-dependence given the lower excitation powers used here.

To demonstrate proof of concept, the present study characterized imaging ensemble UCNPs with the imager. This example demonstrates visualization of UCNP using the chip-based imager by imaging a series of core/shell UCNPs with varying $Yb^{3+}$ and $Er^{3+}$ content to measure emission using either 980 nm or 1550 nm photoexcitation. UCNP cores (8 nm) were synthesized with 20/80, 40/60, or 80/20 $Yb^{3+}/Er^{3+}$ ratios and overgrown with inert 4-nm shells. UCNPs in hexane (with hexane alone serving as the negative control) were excited (pulsed illumination) with 980 nm and 1550 nm, source and imaged with a custom 2,880 pixel array, sized at 55 μm each, implemented in 180 nm technology, externally controlled by an FPGA to accurately manipulate timing.

The effects of excitation ($T_{exc}$) pulse duration on emission signal intensity were assessed. To extract the excitation duration dependency, the UCNPs were excited for increasing durations of time (Texc) and the emission intensity was measured. This duration represents how long the nanoparticles are illuminated with the excitation light source before the start of the time-resolved imaging sequence.

With these nanocrystals in the experimental setup depicted in FIG. 8, in various implementations of the system 10 the initial emission intensity, A·, luminescence lifetime, τ, and total integrated emission count, A·τ, were measured at a given power density (8 W/cm² at either 980 and 1550 nm). Measured decays for varying UCNP compositions range from 600 μs to 1.3 ms at either 980 nm or 1550 nm excitation. These values are longer than measured or calculated, but consistent with UCNP power-dependence given the lower excitation powers used here.

While most $Yb^{3+}/Er^{3+}$ upconversion is nominally a 2-photon process with following 980-nm excitation of the $Yb^{3+2}F_{5/2}$ manifold, 1550 nm excitation of the $Er^{3+4}I_{13/2}$ manifold leads to upconversion via a nominal 3-photon process, for example as shown in FIG. 5A. For all UCNP compositions, NIR-I excitation produces a stronger signal than with NIR-II, consistent with significantly higher efficiency of 2-photon versus 3-photon upconversion processes.

Optimizing UCNP Emission Intensity for Use With Imager. Besides the concentration of the nanoparticles, illumination power and duration affect the emission signal's intensity. The flux of emission photons is, to first order, proportional to the influx of excitation photons and nonlinearities are seen only at very large excitation powers, where the particles start becoming saturated. It important to note that the various implementations of the system 10 are visualizing ensembles of UCNPs at fluences of <1 W/cm², compatible with in vivo use. Increasing the duration of illumination of the UCNPs, during which the imager is off, increases UCNP emission intensity, eventually saturating and reaches its final value near t=5 ms.

Spatial Resolution of Images. Eliminating Optics. Finally, the various implementations of the system 10 eliminate the need for focusing optics, which are challenging to miniaturize while maintaining performance. Optics suffer from fundamental limitations such the significant aberration and imperfections present when fabricating optics at the microscale (and other issues such as ghost images) and miniaturized fluorescence imagers are still several centimeters in length. By placing the imaging chip directly against the tissue itself, an approach called "contact imaging", the micron-proximity of the imager to tumor cells captures light before it diverges—preserving spatial resolution and increasing sensitivity. The various implementations of the system 10 combine high pixel density and in-pixel integration of micro-fabricated angle selective gratings (ASG) for image deblurring (7 μm tall structures integrated directly on photodiodes which the various implementations of the system 10 have demonstrated), to enable single cell resolution, as shown in FIG. 10.

This imager chip is thinned to just 25 μm and back-side coupled to a 100 μm-thin LED for a completely integrated molecular imaging "skin" which is embedded within surgical instrumentation. Connection via a thin flexible wire to an external computer and monitor allows for imaging processing, cell recognition and visualization, such as is shown above in FIG. 6.

The various implementations of the system 10 have demonstrated quantification of cell detection using an integrated circuit-based fluorescence imager, shown in FIGS. 14A-14D. Building on that work, the various implementations of the system 10 have developed a CMOS time-resolved imaging array. Images are obtained with the 2,880 pixel array, implemented in 180 nm technology, externally controlled by an FPGA to accurately manipulate image timing. The closer the imager surface is to the target cells, the higher the sensitivity and spatial resolution. Previously, the various implementations of the system 10 have demonstrated a spatial resolution of ~250 μm imaging cells using the custom fluorescence contact imager with angle-selective gratings however, resolution for fluorescence is limited by the 500 μm optical waveguide and filter required to insert light between the opaque imager and tissue surface.

Figure 14A:
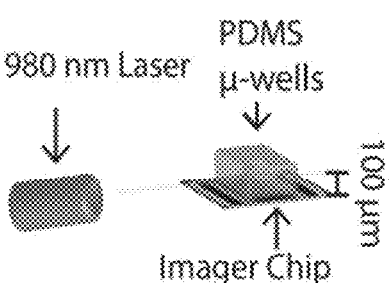
FIG. 14 shows chip imaging of UCNPs. (a) aUCNP-TRI array setup, (b) imaging a 500 um microwell of aUCNPs in a PDMS mold showing sharp features (c-d) Spatial resolution of fluorescence contact imager with ASG, and (e) anticipated improvement in resolution with proposed the imager.
Figure 14B:
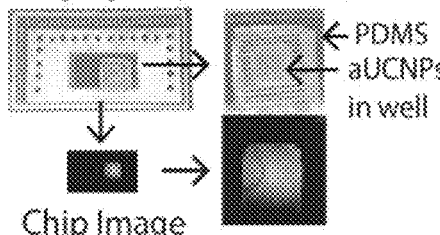
Figure 14C:
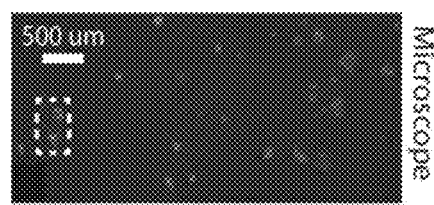
Figure 14D:
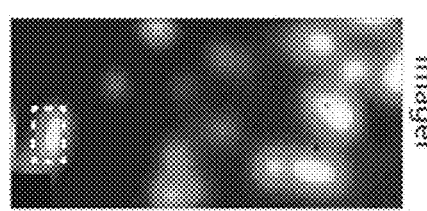
Figure 14E:
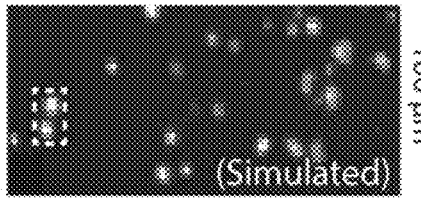

FIG. 14C is simulated data that shows a microscope image, and the corresponding image from the custom sensor, FIG. 14D, of 3D cell cultures. In use, time-resolved imaging and through-illumination eliminates the need for both filters and waveguides, and simulating the same image with separation of just 100 μm (FIG. 14E), the spatial resolution is improved >5×, reducing background and blur and enabling single-cell identification.

Spatial Resolution and Determination of Minimum Detectable Signal. The present examples also demonstrate time-resolved imaging of spatial features with UCNPs in a 500 μm microfabricated well to simulate a focus of labeled cells (FIGS. 14-15). Recognition of small tumor foci amidst a strong and varying background of nonspecific binding and autofluorescence requires accurate background subtraction. Variations in antibody distribution and binding (both within, and between, patients) cannot be predicted a priori, prohibiting the use of a global threshold for MRD and current efforts are limited to centimeter-scale tumor foci. Hence, certain implementations require "local" background measurements, near the tumor cluster, for accurate subtraction and edge detection driving the need for spatial resolution below the millimeter-scale excision achievable by surgery. Alternate implementations do not require background measurements.

Figures 15A, 15B, 15C:
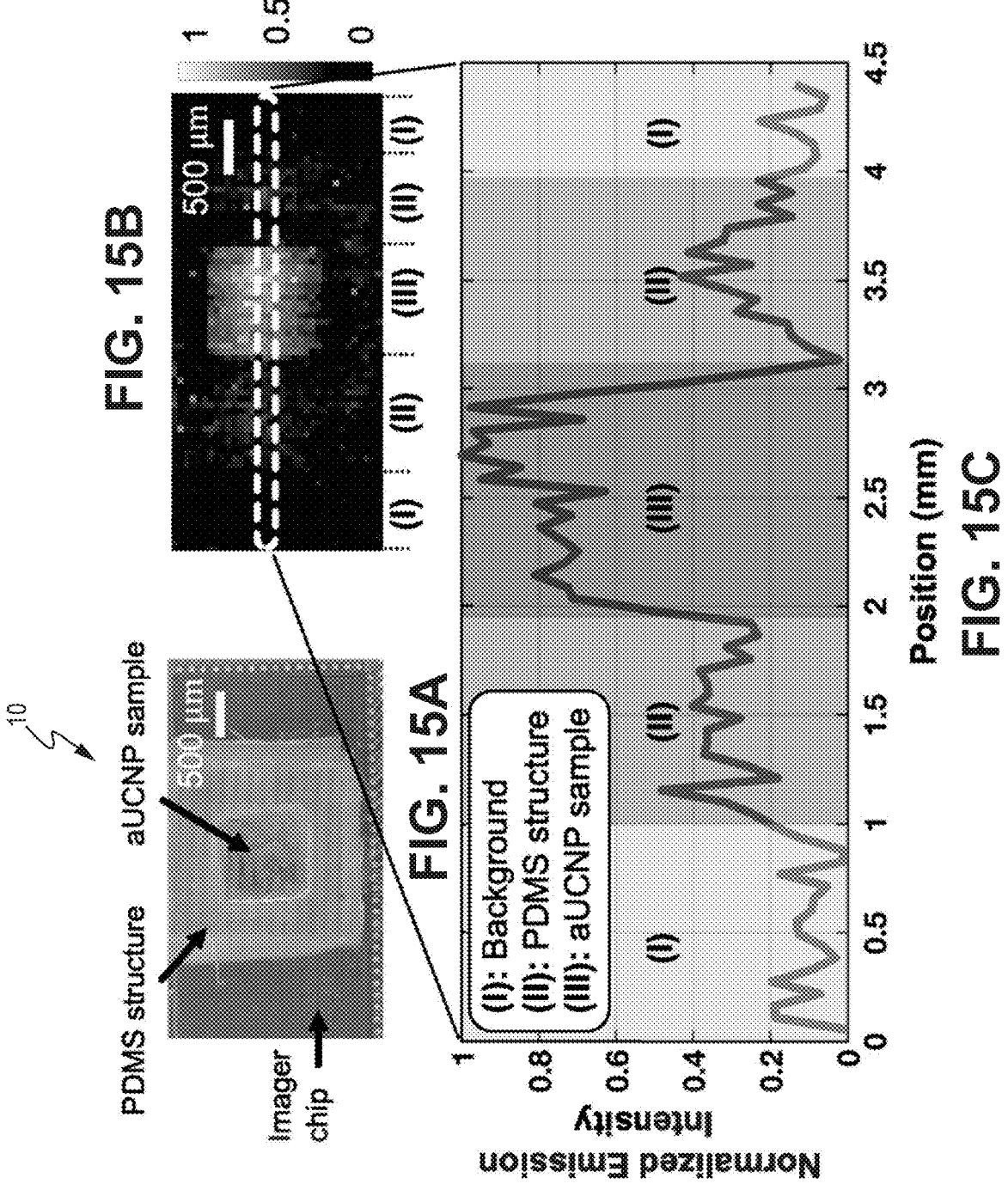
FIG. 15 (A) is a photograph of CMOS contact imager and PDMS micro-well holding UCNPs, fabricated for this study. (B) Time-resolved image of the UCNP-coated surface of the micro-well. Normalized emission intensity shown as in grayscale legend. Section (I) is background, (II) is outer PDMS with UNCPs diffused into PDMS, and (III) is microwell with UCNP sample. (C) Cross-section emission profile for the three regions in (B).

To determine the imaging quality achievable with a 25-micron thin microscope, the implementation of the system 10 shown in FIG. 15A, a 1550 nm excitation source was used to excite the UCNP-coated microstructure and the image was acquired using time-resolved imaging. The custom-fabricated PDMS micro-well and the CMOS imager demonstrate that INSITE is able to resolve the spatial features of the micro-well with nearly single-pixel sharpness (55 μm), translating into a spatial resolution performance sufficient for detecting microscopic residual disease. A cross-section of the acquired signals (shown in FIG. 15B-15C), shows three different regions of the image. Aside from the micro-well and the background, the intermediate zone represents the PDMS surrounding the micro-well. Due to the porosity of the PDMS, small amounts of UCNPs diffuse into the surrounding area, generating a small signal in this area. For a concentration of $10^{12}$ UCNPs per mm², the measured average signal-to-background ratio is 6.5. The background is dominated by the dark pixel current, which can ultimately be subtracted out.

INSITE achieves this spatial resolution without the use of conventional lenses through both proximity to the tissue sample and direct integration of on-chip microfabricated collimators, and is limited only by the pixel size. INSITE uses angle-selective gratings (ASG) to improve spatial resolution with chip-based imaging. ASG are arrays of micro-collimators fabricated directly on each pixel, as described in detail in the incorporated references and in, for example Papageorgiou, E. P., Boser, B., & Anwar, M. (2019). Chip-Scale Angle-Selective Imager for In Vivo Microscopic Cancer Detection. IEEE Transactions on Biomedical Circuits and Systems, using only the inherent metal interconnect layers common to all CMOS process—obviating the need for any postprocessing and not adding any thickness to the imager itself. The versatility of CMOS fabrication technology has led to the on-chip integration of a variety of optical components such as wavelength-selective optical filters that could be tuned to be compatible with quantum dot applications, or stacked diffraction gratings for lensless 3D imaging to reject angled incoming light and decrease blur in the image. Other lensless imaging platforms have also been reported in that leverage computational techniques. As demonstrated here, the elimination of optical filters and focusing optics enables placement of the custom designed INSITE imaging chip directly against the sample itself, capturing light before it diverges, achieving both spatial resolution and increased sensitivity without optics.

Strategies to increase image quality include increasing excitation laser power, and increasing the number of images acquired for averaging. Since various implementations of the system 10 are pulsing light, those various implementations of the system 10 use the time-averaged power, allowing the instantaneous illumination to reach 80 W/cm$^2$ (for short, <10 s, durations). Further approaches are of course possible.

Illuminating at Safe Optical Intensities. To image a single cell with the prototype sensor, certain implementations of the system 10 determine the minimum illumination intensity needed. The number of receptors (e.g. HER2, PSMA) per cancer cell varies from 10$^5$/cell to 10$^7$/cell, thus to be selective these implementations of the system 10 aim at detection of 10$^6$ UCNPs within one pixel. By using short (millisecond) pulses of light, higher instantaneous illumination power can be used, while maintaining low total power delivered. The ANSI (skin exposure) limit for a short 2 ms pulse of 980 nm is 420 W/cm$^2$ (total power 0.85 J/cm$^2$) and 500 W/cm$^2$ (1 J/cm$^2$) for 1550 nm.

Image Recognition. To identify tissue labeled by UCNPs with this imager, the various implementations of the system 10 employ of cell cluster size using an automated cluster recognition algorithm as described in Papageorgiou, E. P., Zhang, H., Giverts, S., Park, C., Boser, B. E., & Anwar, M. (2018). Real-time cancer detection with an integrated lensless fluorescence contact imager. Biomedical Optics Express, 9(8), 3607-3623, or other appropriate image recognition strategy.

Tissue Imaging. As shown in FIGS. 16A-16H, in vivo labeled tissue samples have previously been imaged with an fluorescence-based integrated circuit imager 47-50 and live animal imaging of UCNPs in mammary glands (recapitulating a breast cancer model. The various implementations of the system 10 also have established proof-of-concept for tissue imaging of UCNPs with the custom imager in a breast and prostate cancer model (FIGS. 16A-16B): UCNPs are injected into a mouse bearing a PSMA-expressing LNCaP tumor, imaged (FIG. 16C) and then excised. The excised tumor (and negative control uninjected tumor) are imaged with both the customized live animal imager (FIG. 16E) and imaged (FIG. 16G) at 1550 nm excitation light. The chip readily visualizes UCNPs (FIG. 16H) in the tumor tissue.

Figures 16A, 16B, 16C, 16D, 16E, 16F, 16G, 16H:
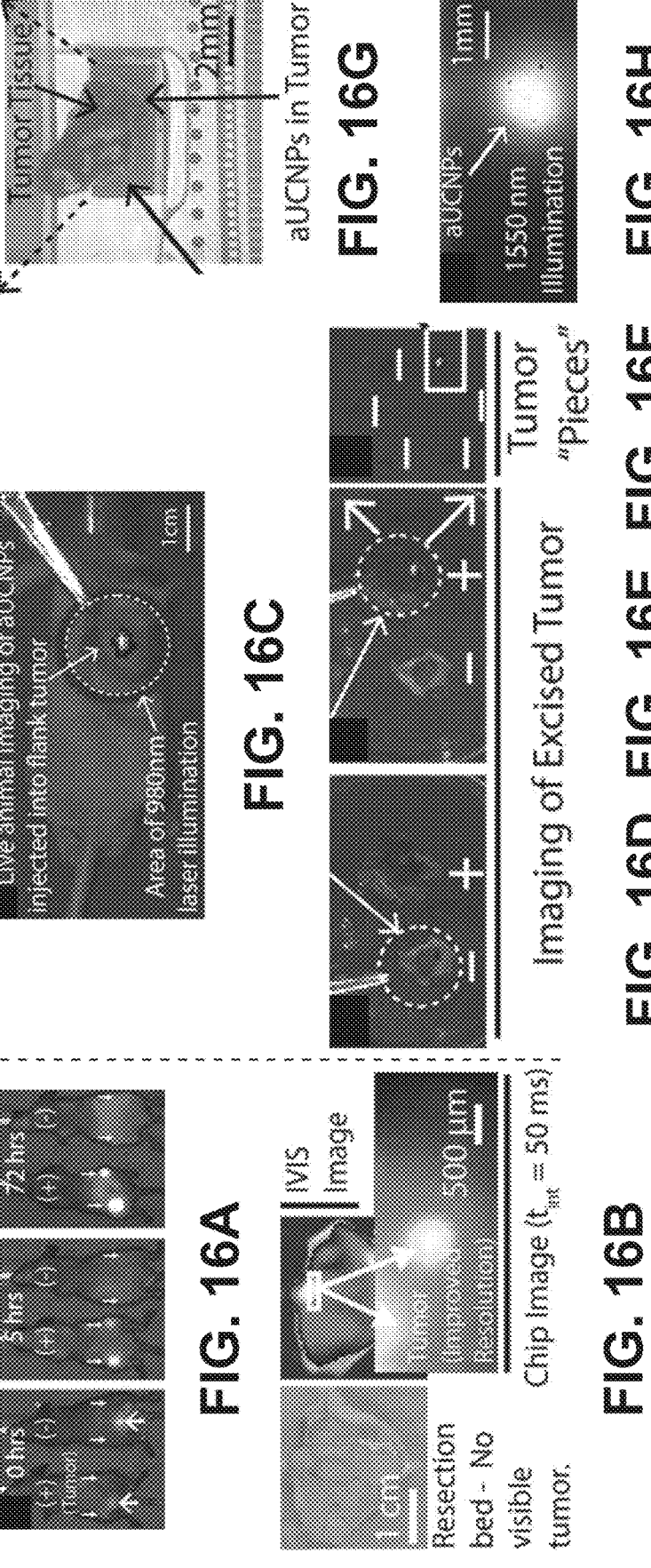
FIG. 16 shows in vivo imaging. (a) Margin imaging We have demonstrated both systemic and intratumoral injections of fluorescently-tagged (IR700DX) Trastuzumab in a HER2+ breast cancer model (left mouse). In (b) a positive margin is identified in real time (<0.05 s) with the fluorescence chip-based imager (confirmed with IVIS imager), despite no visible tumor in the resection bed. (c) Chip imaging of aUCNPs in an in vivo prostate cancer model. LNCaP cells are implanted bilaterally and a single tumor is injected with aUCNPs and visualized with the customized IVIS live animal imager, outfitted with a 980 nm laser, showing aUCNPs in the tumor. Non-injected (−) and injected (+) tumors are excised and imaged (d,e), with the 980 nm laser focused on each one sequentially. No background autofluorescence is seen in the (−) tumor and aUCNPs are visible in the (+) tumor. (f) The (+) tumor is diced in to 6 pieces (underlined); aUCNP containing-tumor (square) is placed on the bare imager chip (g, no lenses, no filters), and illuminated with 1550 nm light. The chip identifies aUCNPs within the tissue (h). Live mouse images of intratumorally-injected NaEr0.8Yb0.2F4 aUCNPs with 8 W/cm2 980 nm excitation. (I) Images of aUCNPs-injected into mouse prostate tumor (left) and non-injected side (right). Emission intensity as in colored legend. (J) Measured emission spectrum of the injected and non-injected sides, showing tumor-specific Er3+ emission bands at 545 and 655 nm
Figure 16I:
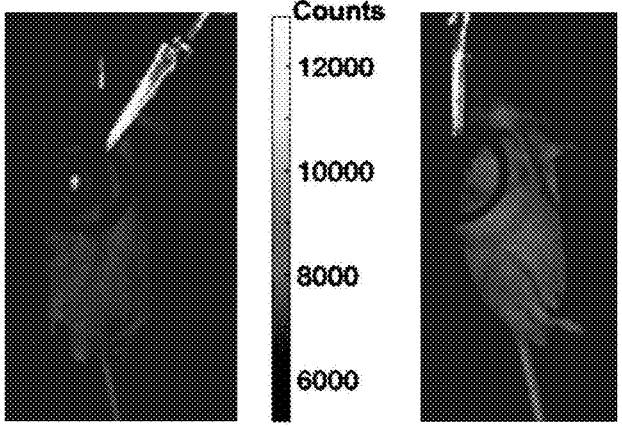
Figure 16J:
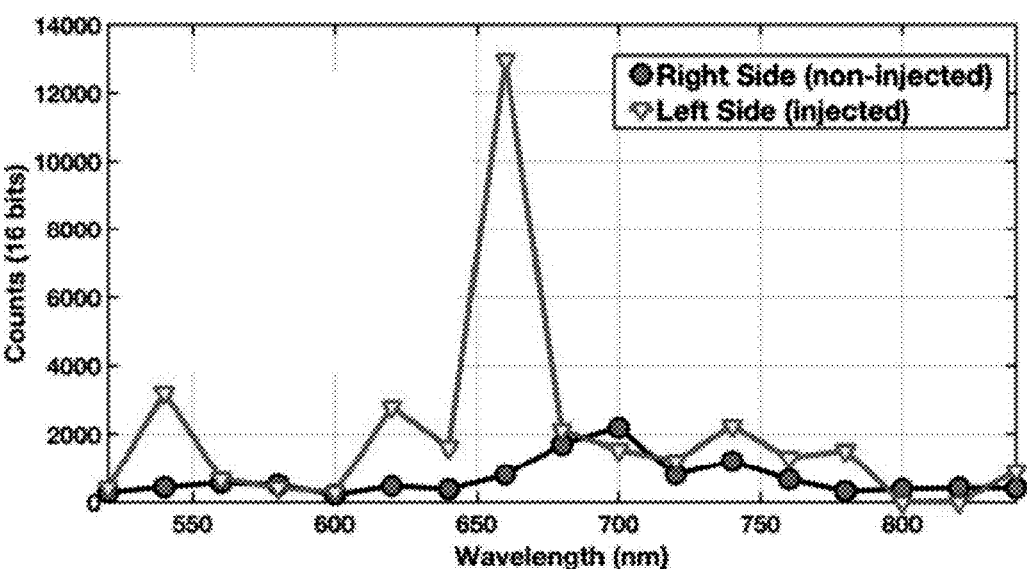

To determine the applicability of the imaging system in tissue imaging, a prostate tumor was injected with aqueous 250 nM polymer-encapsulated 26-nm NaEr$_{0.8}$Yb$_{0.2}$F$_4$ aUNCPs. UCNP-injected mice were imaged a custom-modified IVIS imager using NIR-I illumination, showing colocalization of the tumor and UCNPs. Images of a tumor on the contralateral side of the mouse without UCNP injection shows no measurable visible emission (background dark current only). To ensure UCNPs were being imaged, the spectrum of the acquired emission signal was measured (FIG. 16I-16J), displaying the characteristic emission spectrum of the nanoparticles, with the two major visible emission bands of the UCNPs at 545 nm and 655 nm. Using the UCNP emission band at 650-670 nm, the signal-to-background ratio is 15.

Figure 17:
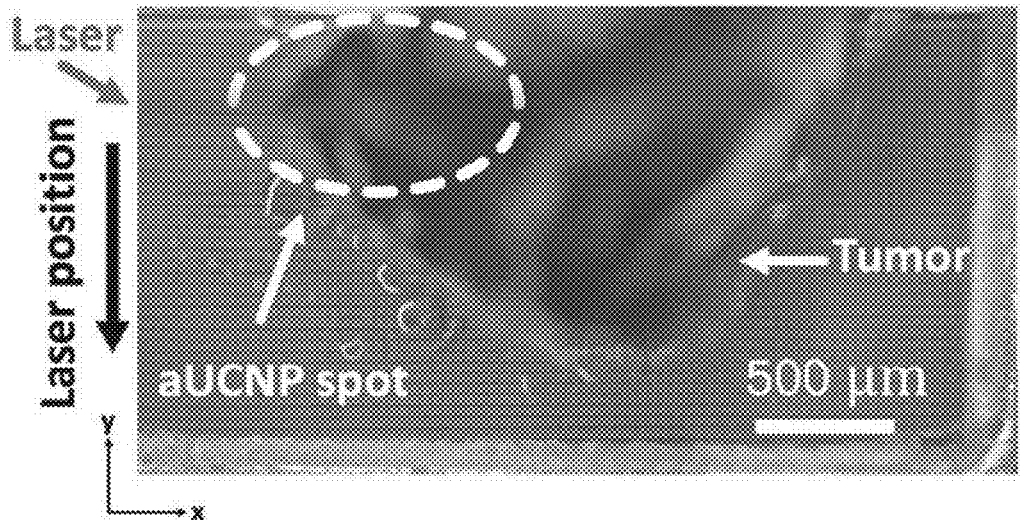
FIG. 17 is on imager. Photograph of the intratumorally-injected tumor sample placed directly on the contact imager.
Figures 18A, 18B:
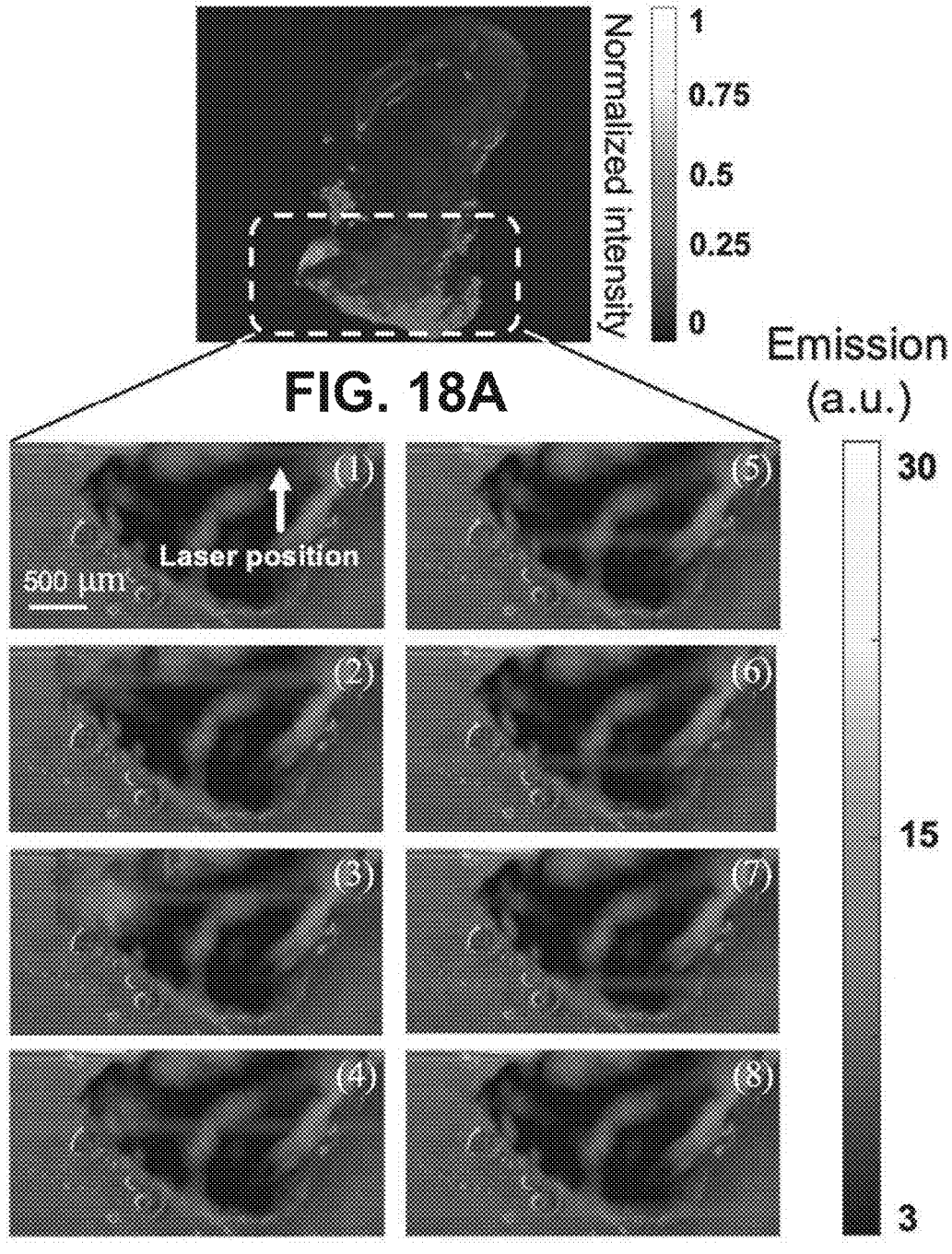
FIG. 18 depicts tumor imaging. (A) is a microscope image of excised tumor injected with 25 μL of a 250 nM aqueous dispersion of UCNPs, excited with 1 W/cm2 980 nm, showing distinct localization of UCNPs. (B) shows images of NIR-II laser scanning of tumor, from top to bottom in increments of 300 μm (numbered 1-8). At each position, an image of the tumor sample is acquired with INSITE using a 5 millisecond-pulsed 60 W/cm2 1550-nm laser for illumination.

To determine if the UCNPs injected into the tumor can be visualized with INSITE alone, the injected tumor was excised and imaged with the INSITE chip imager. FIG. 17 shows a photograph of the excised tumor sample on the 25-micron imaging chip. For reference, the image of the excised tumor on a microscope is shown in FIG. 18A, and the image acquired with INSITE reveals a distinct area of UCNPs in the excised tissue is shown in FIG. 18B, with a signal to background ratio of 9, closely matching the performance of the IVIS imager, which incorporates high performance optical filters and a cooled CCD camera. Results from these experiments demonstrate that the ultra-thin time-resolved CMOS imager, custom designed to image engineered UCNPs, is capable of imaging within tissue, with no background autofluorescence and with little to no additional interference from the excitation light. More extensive work in toxicology and biodistribution with immunotargeted UCNPs will be needed to assess the suitability for these nanoparticles for tumor targeting in mice or human tissue.

Figure 19:
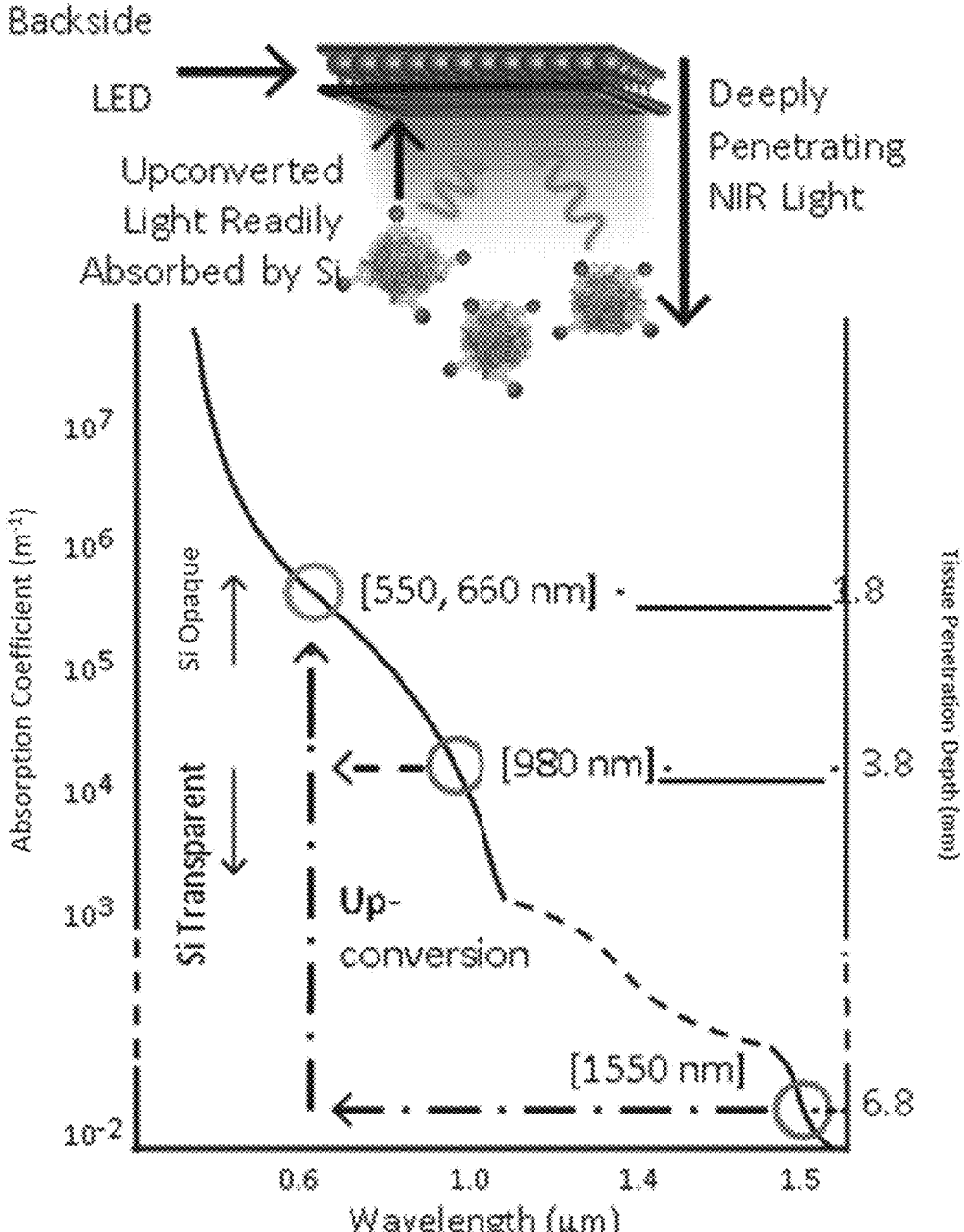
FIG. 19 shows upconversion through-illumination of silicon. 980 and 1550 nm is transmitted through a thin layer of silicon from a back-side attached LED array. Unconverted photons are absorbed by photodiode, producing an image.

Through-Illumination enables UCNP imaging in a single monolithic imaging chip. To fully realize a molecular imaging skin with a contact imager, the tissue surface must be illuminated—however the path to direct illumination is blocked by the imager itself. Strategies such as side illumination introduce additional bulk with integrated LEDs, Laser Diodes or VCSELs; however, silicon itself is transparent in the infrared with a bandgap at 1.1 eV or 1100 nm, as shown in FIG. 19. Illumination in the IR range allows direct penetration through the imager, with a further advantage of deep tissue penetration, but requires up-conversion to ensure that emitted photons interact with the photosensor. Here, the various implementations of the system 10 are configured for light illumination integration with LEDs, Laser Diodes or the like and imagers configured to allow for (a) mitigation of substrate carriers and (b) pixel saturation, generated by high-intensity through-illumination. It will be appreciated that light penetration below the band-gap is exponentially related to silicon thickness, driving the desire for an ultra-thin substrate.

Integrating illumination enables a fully integrated system requiring only ultrathin, flexible wires to communicate power and data—enabling realization of a molecular imaging skin. the preliminary data establishes the feasibility of through illumination, and introduces several technical advances needed to move to illumination powers needed for in vivo imaging.

Through Illumination Using LED or Laser Diode Backside Integration. One option for illumination is to integrate a thin (1 mm or less) LED. Laser Diode, VCSEL, or other light emitting device with NIR (>900 nm, for example either 980 nm or 1550 nm for UCNPs) emission onto the back of the imager to enables a fully integrated solution. The light emitted from the backside of the imager passes through the imager and illuminates the sample (such as tissue) on the other side (imaging side, with photodiodes). In this method, light passes through the imager, and is thus called through illumination. The wavelength of light must be such that the imager material (in this example, silicon) is transparent to it. In the case of silicon, transparency increases with longer wavelength light (such as light above about 900 nm, with improved transparency above about 1100 nm).

Optical power loss must be accounted (for example, up to 50×) due to (1) reflection due to the high index of refraction of silicon and (2) absorption within the silicon, which is exponentially related to silicon thickness. The illumination light can be patterned to improve spatial resolution whereby fine patterns of light are used to illumination the surface, often at a spatial resolution that is finer than the imager itself. The illumination patterns can be sequentially altered and the images taken after each illumination patterned can be mathematically combined to create a higher resolution image. This principle is known as patterned or structured illumination. Here, the patterns can be used as a method for time-resolved imaging, where by each patterned is pulsed one or more images, and the image taken after each pulse.

Reflection on entry to the silicon requires index-matching layers (gels, example ThorLabs G608N3) to optically couple into the chip, reducing optical loss from reflection by 2×. A commercially available LED was affixed to the thinned chip. One such example includes SMBB970D-1100 from Epitex, a 1 mm thick package with 2 W output at 970 nm. This die can be removed from the package and further thinned to achieve ultra-thin monolithic integration (<200 μm).

Substrate carriers are generated by light entering the chip substrate from backside, or through illumination. These carriers drift into the photodiode causing background, indistinguishable from signal, and therefore imaging must occur after these carriers have recommended. The recombination lifetime can be written $t_{life}=W^2/(2*Dn)$ where W is the wafer thickness and Dn is the Diffusion coefficient for electrons (approximately 36 $cm^2$/s in silicon). The strong dependence on wafer thickness stems from carriers recombining at a high rate at the silicon surfaces. Using the first-generation imager, we measured the effect of substrate carriers on pixel output as a substrate thickness, demonstrating decreasing $t_{life}$ as a function of chip thickness ($t_{life}$=75 μs at 25 μm wafer thickness, as shown in FIG. 8C). Recognizing that the LED now represents the dominant thickness of the device, ultra-thin LEDs can be integrated.

FIG. 20 shows device integration, according to one implementation. (a) shows 100 μm-thin microdiodes affixed to the back of the CMOS imager chip (c), which is thinned to 25 μm (b). The resulting molecular imaging "skin" can be affixed to surgical instrumentation, with only thin wires supplying power, data and control signals to the chip. As an example, a scalpel will with imagers on both sides will be developed.

Figures 21A, 21B, 21C:
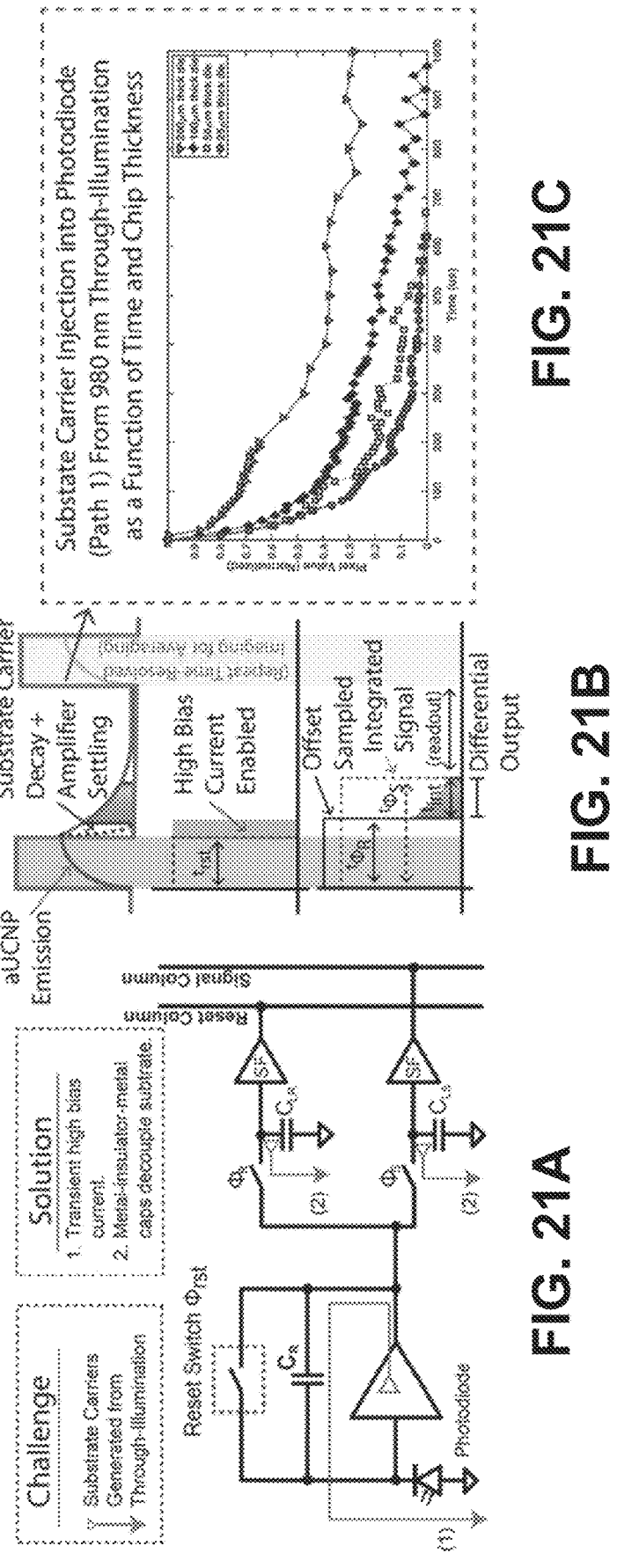
FIG. 21 depicts (a) model chip architecture/in-pixel architecture with substrate carrier artifacts addressed in next gen design to allow 10-40 W/cm2 of through-illumination. (b) time-resolving timing diagram, and (c) measured time constant of thinned imagers, with 25 μm imager showing only a 75 μs substrate carrier time constant, much less than aUCNPs.

Chip Design. Substrate carriers are generated by light entering the chip from backside or high-power through illumination. These carriers drift into the photodiode causing background, indistinguishable from signal, and therefore imaging must occur after these carriers have recommended. The recombination lifetime can be written $t_{life}=W^2/(2*Dn)$ where W is the wafer thickness and Dn is the Diffusion coefficient for electrons (approximately 36 $cm^2$/s in silicon). The strong dependence on wafer thickness stems from carriers recombining at a high rate at the silicon surfaces. Using the first-generation imager, we measured the effect of substrate carriers on pixel output as a substrate thickness, demonstrating decreasing $t_{life}$ as a function of chip thickness ($t_{life}$=75 μs at 25 μm wafer thickness, as shown in FIG. 21C.

Further Imaging Implementations. While the first-generation imager works with through-illumination, a new pixel design is needed for increased through-illumination intensities, as substrate carrier concentrations generated with >0.1 W/$cm^2$ create substrate currents that overwhelm the in-pixel amplifier through diffusion into both the photodiode and MOS-capacitors, used for sample and hold and correlated double sampling. The various implementations of the system 10 imager decouple typical elements from the substrate such as eliminating the MOS-capacitors in favor of metal-insulator-metal capacitors and provide a transiently increased bias current during through illumination to prevent amplifier saturation from the large photodiode current during illumination.

Certain implementations of the chip are constructed and arranged to initially tolerate 40 W/$cm^2$ settling within less than 1 ms to allow for optimal imaging. However standard design techniques can accommodate significantly more power. Challenges with amplifier settling, should it saturate, can be mitigated with a longer delay time ($t_{\Phi R}$), at the cost of lower integrated UCNP signal. An optimized photosensitive CMOS process (X-Fab) with P-I-N diodes can improve responsivity 10×, decreasing integration time.

In further implementations of the imager, the imager is constructed and arranged to decouple circuit and photodiode elements from the substrate such as eliminating the MOS-capacitors in favor of metal-insulator-metal capacitors and provide a transiently increased bias current during through illumination to prevent amplifier saturation from the large photodiode current during illumination.

Certain implementations of the chip make use of PNP photodiodes, whereby the Nwell-Psub acts as a shield from the substrate.

Certain implementations feature switches that couple the photodiode directly to the power supply during illumination to avoid drawing significant current through the amplifier and saturating it. Challenges with amplifier settling, should it saturate, can be mitigated with a longer delay time ($t_{\Phi R}$), at the cost of lower integrated UCNP signal.

Certain implementations replace sample and hold capacitors with substrate independent capacitors (like MOSCaps) to avoid coupling into the substrate. If MOS-Caps must be used, use PMOS devices to shield the transistors from the substrate.

Various implementations feature an optimized photosensitive CMOS process (X-Fab) with P-I-N diodes that can improve responsivity by 10× or more, thereby decreasing integration time.

These designs provide the possibility to allow time-resolved NIR-II and NIR-I excitation of molecularly labelled cancer cells particles using a through-illumination method. This illumination scheme would obviate the use of any light-guiding structures such as lenses, crystals or waveguides conventionally used to properly direct to and focus the excitation light on the target molecules. For example, this could be used for an imager during surgery that was a drop-in probe placed against tissue of interest labeled with an optical nanoparticle and used to image that tissue for nanoparticles.

As such, the various CMOS imagers have been designed to be robust against external and direct NIR excitation by a combination of design modifications. Due to the absorption and sensitivity of Si-based photodiodes to NIR-excitation, unwanted carriers will be generated in the substrate and will introduce interference on the pixel value. The specific type of photodiode used in the design is fabricated using a p+ implant in an n-well sitting in the p-type substrate. The imager array takes advantage of the "p+/n-well" photodiode which is surrounded by another internal photodiode, "n-well/p-sub", which is used to drain the majority of the charges generated due to the NIR excitation during illumination.

It is appreciated that as such, the NIR light is capable of traveling much further, and will therefore generate the majority of the carriers in the p-sub and n-well region and can therefore be drained by a low-resistance path (direct bypass to supply) in the n-well.

After the illumination, the resulting visible emission light from the specimen will be captured and absorbed by the Si-based photodiode, and being visible and quickly absorbed, the majority of the emission light will be absorbed in the p+/n-well photodiode and can be shielded from other interfering carriers in the substrate and n-well.

An additional draining mechanism for generated interfering carriers has been implemented internally in the pixel front-end circuitry, by providing a temporary low-resistance path from the p+ implant to ground to quickly drain and provide recombination current to the small amount of carriers generated in the p+ region as a result of through-illumination.

The internal storage capacitors in the pixel have also been implemented using metal-on-metal (MOM) capacitors, a much more robust alternative to their MOS-type counterparts which are highly sensitive to substrate and carrier disruptions.

Leakage of the internal reset switch in the pixel is also very critical to the linearity and integrity of the output signal and image. To this end, the input switch has been designed to generate a constant and signal-independent leakage, that can be subsequently subtracted and properly cancelled out. Deep integration of the circuits and/or nanophotonics enables a single, monolithic imaging sensor. Leveraging an unprecedented level of integration of electronics and photonics, made possible by the recent introduction of an advanced GlobalFoundries 45 nm SOI process semiconductor manufacturing process, various implementations of the system 10 directly embed illumination at the pixel level to achieve a higher spatial resolution using techniques similar to confocal microscopy. Image resolution is a product of both the pixel density and the spatial illumination patterns. This allows both improved spatial resolution and the ability to retain all illumination and imaging in a single CMOS process, allowing the entire chip to be just 25 microns thin.

Figures 23A, 23B, 23C:
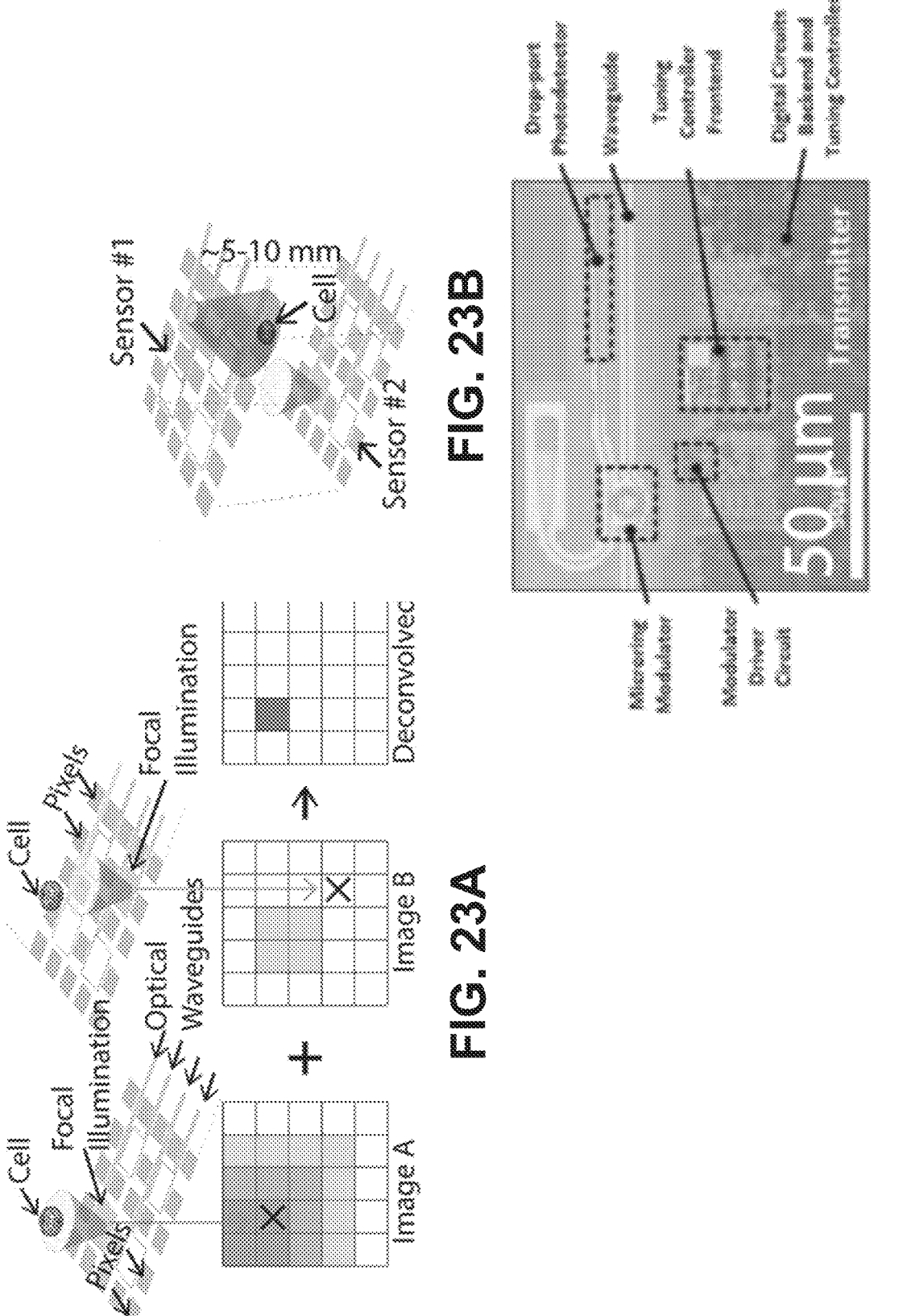
FIG. 23 shows several views of integrated photopnics. (a) Focal illumination at the pixel level, similar in principle to confocal imaging, allows deconvolution of the image for increased resolution. (b) A similar principle can be applied to two sensors facing each other. (c) Example of Global Foundries silicon nanophotnics, with micron-scale photonics integrated with on-chip circuitry.

Typically, illumination is uniform, and resolution is a purely a function of imaging optics and pixel density. Conversely, confocal microscopy uses a low-resolution imager, but precisely defines the illumination pattern, which then defines the spatial resolution. Here, various implementations of the system 10 combine these techniques, matching the pixel size with illumination patterns. With the current pixel size of 55 μm, the goal is illumination precision on this order, and pixel size can be readily reduced below this in modern CMOS processes. Demonstrating the tight integration of electronics and nanofabricated optics, a team recently developed the world's first micro-processor with integrated photonic I/O, featuring 70+ million transistors and thousands of photonic components on the same die. Building on this and illustrating applicably to biosensors the group has developed a chip-based molecular sensor using nanophotonic resonators, as shown in FIG. 23C.

To fully integrate illumination with imaging, with no added thickness, various implementations of the system 10 route photonic waveguides and grating couplers within the pixel array, allowing ultra-fine control over illumination patterns at the pixel level. Sequential illumination (or in patterns) and imaging, as shown in FIG. 23A, enables a higher resolution image along the plane (X-Y) of the sensor to be resolved within tissue. While confocal imaging has been used to image in the sub-cellular regime for table-top microscopes, the goal is to enable cellular level (~10-100 micron) resolution in tissue, sufficient to monitor changes in immune cell concentration and distribution indicative of immune activation. These images can be "deconvolved" to gain improved spatial resolution.

A similar strategy can use structured illumination where patterns of light are displayed on the object (e.g. tissue containing UCNPs), and spatial features that are too fine to be visualized with the native resolution of the imager can be derived from the interference patterns of the illumination pattern and object. This illumination pattern is then rotated, shifted, or otherwise changed, to allow multiple images to convey the full information of the object, including features that are otherwise too fine (small) to be detected by the imager using uniform illumination.

To improve resolution in the (Z) plane perpendicular to the sensor, opposing sensors are placed facing one-another with a spacing ~5 mm and image simultaneously. At 700-800 nm illumination, common to clinically used near infrared dyes, light penetrates ~5 mm (with 0.5% of light remaining), allowing the same cells to be imaged by both sensors, enabling reconstruction of a 3-D image, as shown in FIG. 23.

The various implementations of the system 10 can also use a technique similar to light sheet microscopy, whereby the illumination light is focused on a specific plane of the tissue and rastered through it. Similarly, certain implementations of the system 10 can use a technique like confocal microscopy, whereby light is focused at a single point and the image is reconstructed.

Various implementations feature enhancements for single cell imaging. Various implementations feature one or more of the following features or improvements: (1) safely increasing the optical illumination power by taking advantage of increased power allowance for pulsed light versus continuous illumination, (2) decreasing the distance from the photodiodes on the imager surface from millimeters to microns, (3) increasing intrinsic photodiode sensitivity by 10× through the use of an improved CMOS process, (4) lowering imager noise 2×, and (5) decreasing pixel size for improved spatial resolution.

Table 1 depicts improvements in SNR and minimum number of UCNPs detectable with next generation imager. Image time: 2 ms illumination, 2 ms readout. Single cell imaging with just 25,000 UCNPs/cell is possible at 980. It is appreciated that American National Standards Institute limits for a 2 millisecond pulse.

To image single-cells directly within tissue, the system 10 represents a new imaging technology, that directly integrates into an ultra-thin, planar form-factor, that is embedded directly on surgical instrumentation, transforming the tool itself into a single-cell molecular imager (FIG. 9) to guide precision cancer surgeries and biopsies.

The various implementations of the system 10 therefore relate to a fully integrated molecular imaging system through synergistic integration of immunotargeted UCNPs and a custom optics-free, high-sensitivity time-resolved integrated circuit. Enabled by the unique optical properties of UCNPs, the various implementations of the system 10 eliminate or miniaturize each component of a conventional fluorescence microscope, resulting in an ultra-thin planar, imaging surface with single-cell sensitivity requiring only thin, flexible wires to connect it to an external computer and monitor for data processing and visualization.

With increased illumination intensity and closer placement of the tissue sample to the imager surface, the various implementations of the system 10 expect detection of a single HER2+ breast cancer cell ($10^6$ UCNP/cell). Imaging though both blood and tissue is addressed in the previous work, showing only a 6 dB loss (and therefore visible with 980 nm illumination) through an opaque 250 um thick layer of blood. In alternate implementations, SNR of cells labeled with immunotargeted UCNPs can also be performed in vitro with 3D cell culture models.

To achieve single-cell sensitivity for a wide range of cells, including those with low surface tumor marker expression, the various implementations of the system 10 improve sensitivity and spatial resolution. The various implementations of the system 10 only require spatial resolution such that any non-specific background integrated within a single pixel does not mask the signal from the tumor cell. Thus, the various implementations of the system 10 do not require resolution of individual cells. Increased sensitivity allows for lower illumination power, and detection of single cells using a lower concentration of UCNPs delivered to the patient. The various implementations of the system 10 improve sensitivity through using a CMOS technology process with a 10× higher photon sensitivity. The various implementations of the system 10 improve spatial resolution by combining the in-pixel angle selective gratings for image deblurring and reduction of pixel size to 20 μm×20 μm, approaching the size of single cell (10-15 μm). Pixel sizes can however be made to be less than 1×1 um^2.

Reduction in pixel size 4× to 20 μm×20 μm will improve spatial resolution 4×. Placement of the cell <100 μm from the surface increases resolution by an additional 5× (total 20×). Optical sensitivity is increased 10× (0.5 NW) by fabricating the sensor in an IC technology process optimized for photodetection (XFAB Foundry) (SNR+10 dB) using PIN photodiodes, as opposed to the relatively low-efficiency photodiodes (0.05 A/W) in the current 0.18 μm TSMC mixed signal process. Since the functional portion of the imager is contained within the superficial 10 μm, chips are then thinned to 25 μm (a procedure readily done with integrated circuits, as demonstrated in the above.

To achieve a completely integrated, standalone package, certain implementations of the system 10 affix 300 μm×300 μm×100 μm thin LEDS (Rothiner LaserTechnik, CHIP-980-P50) to the chip backside—illuminating directly through the chip, eliminating the need for waveguides or fiber optics. At 980 nm, these commercially available components produce 75 W/cm$^2$ [68 mW/(300 μm)$^2$]. These LEDs can be used, but require averaging of multiple images (for example 6 images with an LED of power 75 W/cm$^2$ is equivalent to a single image of 400 W/cm$^2$). Similarly, 1550 nm LEDs (Seminex, CHP-124) produce 22 W/cm$^2$ (pulsed versions reach up to 200 W/cm$^2$, CHP-157). Aided by angle selective gratings, the new higher sensitivity imager achieves a total of 20× increase in spatial resolution to 12 μm for single cell resolution.

Thinning the prototype imager to 25 μm, the various implementations of the system 10 have demonstrated through illumination at 1550 and 980 nm. Increased sensitivity allows reduction (10X) in illumination power. The various implementations of the system 10 anticipate detection of a single cell with only 25×10$^3$ immunotargeted UCNPs for ultrasensitive detection—expanding use to a wide array of cell types.

No appreciable interaction of light with silicon is observed at 1550 nm, as the characteristic absorption depth is ~100 m, however some background is generated at 980 nm (absorption depth 100 um). Contribution of 980 nm induced background through use of (1) a new diode structure (P-N-P) that shields the detector from substrate carriers, and (2) a transient current "sink" that drains any substrate charge before imaging. Microfabricated mirrors can be added to redirect LED output light. These features are discussed above Given the sub-micron features of modern CMOS processes, reduction of pixel size to 20 μm is readily achieved. Fill-factor is reduced (due to the in-pixel amplifier) from 85% currently, to 70%. However, this translates into an interpixel distance of <5 μm, and therefore all cells will be at least partially captured by a pixel. Power consumption (currently just 3.5 mW) will increase by 4×, but well within acceptable limits (14 mW).

Integrated Surgical Tools for Real-Time Cell Imaging with Immunotargeted UCNPs. The various implementations of the system 10 require an imager that can be used during surgery that is sufficiently small and is compatible with existing methods, and require minimal disruption to clinical practice. Several instantiations of the device can be envisioned. For example, one approach is to embed the imager along a biopsy needle and scalpel, as both of these instruments are used in surgery and thus can be easily integrated. This will be done by custom fabricating the imager in a form-factor that covers the surface of a scalpel blade; the various implementations of the system 10 then affix an imager to each side, with only a set of thin wires running along the handle for power supply and data transfer. Made in batch, CMOS technology is extremely low cost, allowing these devices to be single-use, disposable items. Other implementations include direct integration on a probe surface, thinning the device enough to be flexible and fitting on a curved surface, mounting on multiple sides of a probe, attaching to a robotic instrument, and directly integrating into surgical gloves.

3D Positional Sensing. Various implementations incorporate a method of recording the real-time position of the imager so that the three dimensional spatial coordinates of each image gathered is recorded. These images are then assembled in real-time to create a three-dimensional construct of the tissue or surface imaged.

The position sensor can be incorporated using CMOS compatible techniques, such as inclusion of an accelerometer and gyroscope on chip, or packaged separately and attached to the imaging chip. Additionally, or alternatively, the probe (or device/platform that the chip is mounted to) can record positional information, through either attachment of a position sensor (combination of accelerometer and gyroscope) or markers/fiducials attached to the device that allow registration in 3D space.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the term "subject" refers to the target of administration, e.g., an animal. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects.

Although the disclosure has been described with reference to preferred embodiments, persons skilled in the art will recognize that changes may be made in form and detail without departing from the spirit and scope of the disclosed apparatus, systems and methods.

27

TABLE 1

SNR.

| | Current | | Anticipated | | ΔSNR (dB) | |
|---|---|---|---|---|---|---|
| | 980 | 1550 | 980 | 1550 | 980 | 1550 |
| Image time | 4 ms | | 4 ms | | | |
| Spatial Resolution | 250 μm | | 12 μm | | | |
| Cell to sensor distance | 2 mm | | <0.05 mm | | +31 | |
| *Power (W/cm², 2 ms) | 6 | 65 | 420 | 500 | +19 | +9 |
| Optical Sensitivity | 0.05 A/W | | 0.52 A/W | | +10 | |
| Cells Imaged | $1 \times 10^7$ | | 1 | | −70 | |
| Noise Reduction | | | | | 6 | |
| Baseline SNR | 26 dB | 23 dB | | | | |
| SNR for Single Cell ($10^6$ UCNPs/cell) | | | | | 22 | 9 |
| Min UCNPs de-tectable (SNR = 6 dB) | | | | | 25K | 500K |

Improvements in SNR and minimum number of UCNPs detectable with the imager. Image time: 2 ms illuminati ms readout. Single cell imaging with just 25,000 UCNPs/cell is possible at 980.
*American National Standards Institute limits for a 2 millisecon pulse.

What is claimed is:

1. An imaging system, comprising:
   a. an imaging chip comprising a silicon substrate and a plurality of pixels, the imaging chip being configured for through-illumination with light transmitted through the silicon substrate, wherein the imaging chip comprises circuitry configured to mitigate or compensate for electrical interference generated in the silicon substrate by illumination passing through the substrate; and
   b. a composition comprising at least one optical nanoparticle wherein the imaging chip is constructed and arranged to detect light emission from the at least one nanoparticle, wherein the at least one nanoparticle comprises an upconverting nanoparticle (UCNP) that upconverts near-infrared light to higher energy light.

2. The imaging system of claim 1, wherein the imaging chip is configured for time-resolved imaging.

3. The imaging system of claim 2, wherein the imaging system further comprises an illumination device.

4. The imaging system of claim 1, wherein the imaging chip is filterless.

5. The imaging system of claim 1, wherein the at least one optical nanoparticle has a luminescence lifetime greater than 1 microsecond.

6. The imaging system of claim 1, wherein the at least one optical nanoparticle has a luminescence lifetime greater than 10 microseconds.

7. The imaging system of claim 1, wherein the imaging chip is lensless.

8. The imaging system of claim 1, wherein the imaging chip is between about 25 microns and about 1 mm thick.

9. The imaging system of claim 1, wherein the imaging chip is between about 1 mm^2 and about 40 cm^2 wide.

10. The imaging system of claim 1, wherein the imaging chip is fitted to a medical device.

11. The imaging system of claim 10, wherein the medical device is a scalpel, probe, drop in probe for laparoscopic or robotic surgery, or glove.

12. The imaging system of claim 1, further comprising an illumination array.

13. The imaging system of claim 12, wherein the illumination array is an array of LED or laser diodes surrounding the chip.

14. The imaging system of claim 12, wherein the illumination array is an array of LEDs, laser diodes, or fiber optics configured for through illumination.

15. The imaging system of claim 12, wherein the through illumination is patterned.

16. The imaging system of claim 1, wherein the optical nanoparticle is conjugated to a molecule targeted toward a cell type of interest.

17. The imaging system of claim 16, wherein the molecule is a protein, antibody, component of an antibody, or small molecule.

18. The imaging system of claim 17, wherein the cell type of interest is a cancer cell.

19. A method of imaging disease tissue, comprising:
   a) introducing a composition comprising at least one optical nanoparticle into tissue, wherein the at least one nanoparticle comprises an upconverting nanoparticle (UCNP) that upconverts near-infrared light to higher energy light;
   b) illuminating the at least one optical nanoparticle via through-illumination of an imaging chip comprising a silicon substrate, the illuminating comprising illuminating with a pulse of light directed through the silicon substrate of the imaging chip, the light having a wavelength in the near-infrared or infrared range;
   c) mitigating substrate carriers generated in the silicon substrate; and
   d) after the pulse of near-infrared light has ceased, recording luminescence of the at least one optical nanoparticle with an imaging chip.

20. The method of claim 19, wherein the at least one optical is illuminated at a first wavelength and emits light at a second wavelength.

21. The method of claim 20, wherein the illumination wavelength is longer than the emitted wavelength.

22. The method of claim 19, wherein the luminescence is recoded after the at least one optical nanoparticle is illuminated.

23. The method of claim 19, further comprising performing ratiometric imaging to determine the depth of the at least one optical nanoparticle.

24. The method of claim 19, wherein at least one optical nanoparticle is conjugated to a molecule or protein that binds to a target cell.

25. The method of claim 19, wherein the protein is an antibody or derivative.

26. An imaging system, comprising:
   a. an imaging chip comprising a silicon substrate and a plurality of pixels, the imaging chip being configured for through-illumination with light transmitted through the silicon substrate, wherein the imaging chip comprises circuitry configured to mitigate or compensate for electrical interference generated in the silicon substrate by illumination passing through the substrate; and
   b. a composition comprising at least one optical nanoparticle wherein the imaging chip is constructed and arranged to detect light emission from the at least one nanoparticle, wherein the imaging system is lensless.

* * * * *